United States Patent
Blanchard et al.

(10) Patent No.: US 10,190,094 B2
(45) Date of Patent: Jan. 29, 2019

(54) METHODS AND COMPOSITIONS RELATED TO INDUCED SENSORY NEURONS

(71) Applicants: THE SCRIPPS RESEARCH INSTITUTE, La Jolla, CA (US); Joel W. Blanchard, San Diego, CA (US); Kevin T. Eade, La Jolla, CA (US); Kristin Baldwin, La Jolla, CA (US)

(72) Inventors: Joel W. Blanchard, San Diego, CA (US); Kevin T. Eade, La Jolla, CA (US); Kristin Baldwin, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 15/106,460

(22) PCT Filed: Dec. 19, 2014

(86) PCT No.: PCT/US2014/071528
§ 371 (c)(1),
(2) Date: Jun. 20, 2016

(87) PCT Pub. No.: WO2015/095718
PCT Pub. Date: Jun. 25, 2015

(65) Prior Publication Data
US 2016/0333311 A1    Nov. 17, 2016

Related U.S. Application Data

(60) Provisional application No. 61/918,965, filed on Dec. 20, 2013.

(51) Int. Cl.
*C12N 5/0793* (2010.01)
*A61K 35/30* (2015.01)

(52) U.S. Cl.
CPC ............. *C12N 5/062* (2013.01); *A61K 35/30* (2013.01); *C12N 2501/13* (2013.01); *C12N 2501/60* (2013.01); *C12N 2506/02* (2013.01); *C12N 2506/13* (2013.01); *C12N 2506/1307* (2013.01); *C12N 2506/45* (2013.01); *C12N 2510/00* (2013.01)

(58) Field of Classification Search
None
See application file for complete search history.

(56) References Cited

U.S. PATENT DOCUMENTS

| 7,446,205 B2 | 11/2008 | Ennifar et al. |
| 7,547,712 B2 | 6/2009 | Ennifar et al. |
| 2013/0022583 A1* | 1/2013 | Wernig ............... C12N 5/0619 424/93.7 |
| 2013/0183674 A1 | 7/2013 | Studer et al. |

FOREIGN PATENT DOCUMENTS

WO    WO2015085201 A1    6/2015

OTHER PUBLICATIONS

Wiggins, et al. (2004) "Interaction of Brn3a and HIPK2 mediates transcriptional repression of sensory neuron survival", The Journal of Cell Biology, 167(2): 257-67.*
Blanchard, et al. (2015) "Selective conversion of fibroblasts into peripheral sensory neurons", Nature Neuroscience, 18(1):25-37.*
Kondo, et al. (2011) "Wnt signaling promotes neuronal differentiation from mesenchymal stem cells through activation of Tlx3", Stem Cells, 29(5): 836-46.*
Hohenauer, et al. (2013) "The neural crest transcription factor Brn3a is expressed in melanoma and required for cell cycle progression and survival", EMBO Molecular Medicine, 5(6): 919-34.*
Quan, et al. (2004) "of neural precursor selection: functional divergence of proneural proteins" Development, 131: 1679-86.*
Lin, et al. (Nov. 29, 2012) "Efficient Lentiviral Transduction of Human Mesenchymal Stem Cells That Preserves Proliferation and Differentiation Capabilities", Stem Cells Translational Medicine, 1: 886-97.*
Akhmetshina, et al. (2012) "Activation of canonical Wnt signaling is required for TGF-[beta]-mediated fibrosis", Nature Communications, 3:735 (12 pages)).*
EPO Communication, dated May 18, 2017, Supplementary European Search Report.
Chambers, et al., Combined small molecule inhibition accelerates developmental timing and converts human pluripotent stem cells into nociceptors.
Lee, et al., Human Sensory Neurons Derived from Induced Pluripotent Stem Cells Support Varicella-Zoster Virus Infection.

* cited by examiner

*Primary Examiner* — Robert M Kelly
(74) *Attorney, Agent, or Firm* — Hugh Wang; Thomas Fitting

(57) ABSTRACT

This invention provides methods of generating induced sensory neurons (iSNs) from non-neuronal cells such as fibroblasts. The invention also provides methods of using iSNs in various therapeutic or non-therapeutic applications, e.g., methods to identify agents or cellular modulations that enhance iSN formation from non-neuronal cells.

9 Claims, 10 Drawing Sheets

METHODS AND COMPOSITIONS RELATED TO INDUCED SENSORY NEURONS

CROSS-REFERENCE TO RELATED APPLICATIONS

The subject patent application claims the benefit of priority to U.S. Provisional Patent Application No. 61/918,965 (filed Dec. 20, 2013). The full disclosure of the priority application is incorporated herein by reference in its entirety and for all purposes.

BACKGROUND OF THE INVENTION

Sensory neurons of the dorsal root ganglia (DRGs) and trigeminal nerve can detect environmental changes through projections in the skin. These neurons comprise three main classes devoted to nociception/puritoception, mechanosensation and proprioception. Nociception is the process by which noxious stimuli such as heat and touch cause the sensory neurons (nociceptors) in the skin to send signals to the central nervous system. Puritoception is the perception of itch. Mechanosensation is the detection of pressure, and proprioception is the detection of muscle movement through the monitoring of muscle stretch. The control of pain, itch and disorders that affect various types of sensory neurons has long been a major challenge for pharmacotherapy. It was reported that at least 116 million Americans and 35% of the population worldwide suffer from chronic neuropathy or pain (Elzahaf et al., Curr. Med. Res. Opin. 28, 1221-1229, 2012). However, only 30% of patients in chronic pain respond to "gold standard" FDA approved treatments (Finnerup et al., Pain 150, 573-581, 2010). Laboratory studies have demonstrated a large range of inter-individual variation in response to identical pain stimuli. Furthermore, it is becoming increasingly recognized that genetic factors are a major contributor to pain phenotype and response to pharmacological treatments. Despite these findings, much pain related drug discovery has relied on animal models, which are unlikely to be useful in modeling subtle differences between humans and have lower throughput than in vitro screens. These factors may help to explain the staggeringly high rates of attrition during clinical trials for even promising preclinical candidates. The control and detection of itch is poorly understood and also a significant unmet medical need. Although cadaveric human sensory neurons are available for research, these cells cannot be genetically altered and have limited availability.

There is a need in the art for effective means for generating functionally responsive sensory neurons in vitro in sufficient numbers for mechanistic studies or drug screening. The present invention is directed to this and other unmet needs in the art.

SUMMARY OF THE INVENTION

In one aspect, the present invention provides methods for generating induced sensory neurons (iSNs). The methods entail co-expressing in a non-neuronal cell a combination of Brn3AlNgn1 (BN1) genes or Brn3AlNgn2 (BN2) genes. Typically, expression of the Brn3AlNgn1 genes or Brn3AlNgn2 genes in the non-neuronal cell is temporal. In some methods, the Brn3AlNgn1 genes or Brn3AlNgn2 genes are transiently expressed in the non-neuronal cell. For example, the Brn3AlNgn1 genes or Brn3AlNgn2 genes can be expressed in the cell via an inducible expression system such as inducible expression vectors. In some methods, the non-neuronal cell for conversion into a sensory neuron is a fibroblast, an embryonic stem cell (ESC), or an induced pluripotent stem cell (iPSC). In some methods, the non-neuronal cell is an embryonic fibroblast or an adult fibroblast. Some methods of the invention are directed to inducing sensory neuron formation from mammalian fibroblast, e.g., fibroblast derived from human, mouse or rat. In some methods, the Brn3A gene and the Ngn1 gene are co-expressed in the non-neuronal cell. In some other methods, the Brn3A gene and the Ngn2 gene are co-expressed in the non-neuronal cell. In some methods, an expression vector harboring the Brn3A gene and the Ngn1 or Ngn2 gene is introduced into the non-neuronal cell. For example, a lentiviral vector expressing the BN1 or BN2 genes can be used for inducing the non-neuronal cell. Some methods of the invention additionally involve examining the induced sensory neurons for the presence of one or more neuronal markers.

In some related embodiments, the invention provides induced sensory neurons generated in accordance with the methods described herein. In some other embodiments, the invention provides isolated cells that harbor one or more expression vectors that express a combination of Brn3AlNgn1 genes or Brn3AlNgn2 genes. Some of these cells are non-neuronal cells. For example, the cell can be a fibroblast, an embryonic stem cell (ESC), or an induced pluripotent stem cell (iPSC). In some embodiments, the cell is an embryonic fibroblast or an adult fibroblast. In some preferred embodiments, the fibroblast is derived from a mammal, e.g., human, mouse or rat. In some of the cells, the expression vectors co-expressing the Brn3AlNgn1 genes or Brn3AlNgn2 genes are lentiviral vectors. In some embodiments, the expression vectors are inducible vectors.

In another aspect, the invention provides methods for treating in a subject a neurological condition or disorder that is associated with or mediated by a loss or degeneration of sensory neurons. The methods entail (1) obtaining a population of non-neuronal cells from the subject in need of treatment; (2) generating a population of induced sensory neurons (iSNs) from the non-neuronal cells by co-expressing in the non-neuronal cell a combination of Brn3AlNgn1 genes or Brn3AlNgn2 genes; and (3) administering a therapeutically effective amount of the iSN population to the subject. Typically, the non-neuronal cells transiently express the Brn3AlNgn1 genes or Brn3AlNgn2 genes. In some methods, expression of the Brn3AlNgn1 genes or Brn3AlNgn2 genes in the non-neuronal cell is temporal. In some embodiments, the non-neuronal cells are fibroblast, embryonic stem cells (ESCs), or induced pluripotent stem cell (iPSCs). In some preferred embodiments, the subject is human, and the non-neuronal cells are human fibroblast. In some methods, the Brn3AlNng1 genes or Brn3AlNgn2 genes are introduced into the non-neuronal cells via a lentiviral vector.

In another aspect, the invention provides methods for identifying an agent or cellular modulation that stimulates conversion of a non-neuronal cell into an induced sensory neuron (iSN). These methods entail (1) co-expressing in a non-neuronal cell (1) a Brn3A gene and (2) a Nng1 or Ngn2 gene in the presence of candidate compounds or cellular manipulations, and (2) detecting enhanced iSN conversion from the non-neuronal cell that has been subject to contact with a specific candidate compound (or subject to a specific cellular manipulation) relative to iSN conversion from the non-neuronal cell that has not been subject to contact with the specific candidate compound (or subject to the specific cellular manipulation). The methods allow identification of the specific candidate compound (or cellular manipulation) as an agent that stimulates conversion of a non-neuronal cell into an induced sensory neuron. Typically, expressions of the Brn3AlNgn1 genes or Brn3AlNgn2 genes in the non-neuronal cells are transient. In some preferred embodiments, expression of the Brn3AlNgn1 genes or Brn3AlNgn2 genes is temporally controlled (e.g., via using inducible expression vectors). In some methods, the candidate compounds to be screened are transcription factors or miRNAs. Some other methods are directed to screening cellular manipulations such as epigenetic modulations of the non-neuronal cell. In some methods, the non-neuronal cell used in the screening is a fibroblast, an embryonic stem cell (ESC), or an induced pluripotent stem cell (iPSC). For example, some screening methods of the invention employ an embryonic fibroblast or an adult fibroblast, e.g., a mammalian fibroblast derived from human, mouse or rat. In some preferred embodiments, the Brn3AlNgn1 genes or Brn3AlNgn2 genes are introduced into the non-neuronal cell via a lentiviral vector.

A further understanding of the nature and advantages of the present invention may be realized by reference to the remaining portions of the specification and claims.

Mitotic inhibition does not significantly decrease the number of neurons generated by BN1 or BN2. Bars are means of two replicate experiments. Error bars are SEM. (g) Quantification of Map2/Tuj1 positive cells induced from tail-tip fibroblasts. (h) BN1 and BN2 induce neural cells from TTFs that stain for somatic sensory markers. Scale bar: 25 µm.

Figure 6:
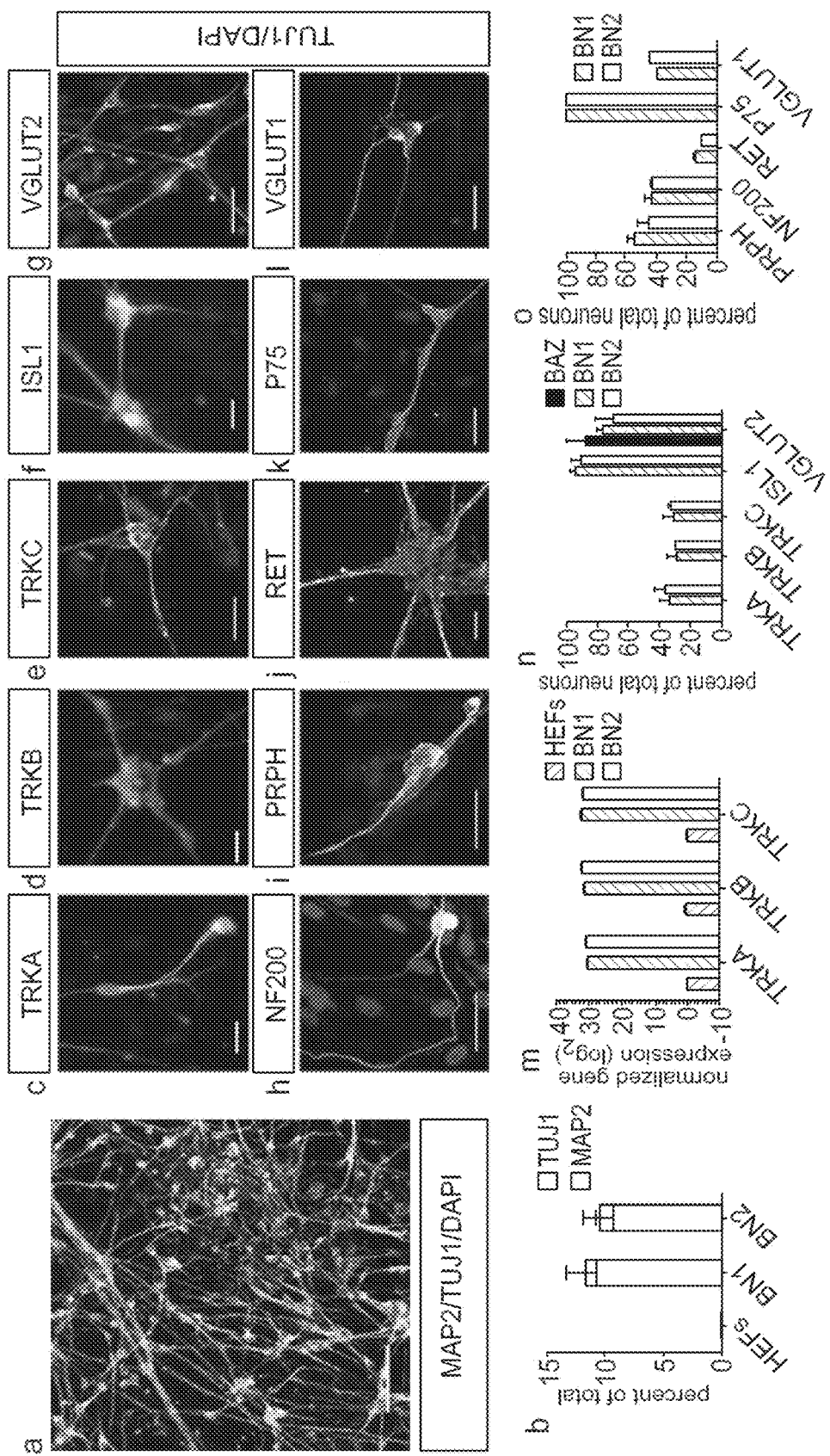

FIGS. 6A-6O show that human iSNs are generated using BN1 and BN2. (a) Expression of BN1 and BN2 converts human embryonic fibroblasts to MAP2/TUJ1 double positive cells with neuronal morphologies 14 days after induction, dox was removed on day 8. Scale bar: 100 µm (b) percent TUJ1 single positive (grey) and MAP2/TUJ1 double positive cells generated from HEFs in BN1, BN2, and rtTA control conditions. (c-1) Neurons induced with BN1/2 express somatic sensory markers Scale bar: 25□□m. (m) Quantitative RT-PCR of TRK receptors in MEFs and iSNs generated with BN1 or BN2. Expression levels are normalized to MAP2. Bars and error bars represent means and SEMs from two independent biological replicates. (n) Quantification of TUJ positive cells expressing TRKA, B, C, VGLUT2 and ISL1 in BN1, BN2, BAZ and rtTA control conditions. (o) Quantification of TUJ positive cells expressing NF200, PRPH, and RET in BN1 and BN2. Error bars represent SEM.

FIGS. 7A-7I show that human iSNs posses functional properties of sensory neurons (a,b) Representative traces of Na/K currents and evoked action potential in BN1 and BN2 iSNs. (c) PCR analysis showing presence of ligand gated calcium channels TRPA1, TRPM8, TRPV1, and voltage gated sodium channel $Na_v1.7$ in BN1 and BN2 human iSNs compared to BAZ and uninfected controls (HEFs) at 16 days post induction. BN1, BN2, and BAZ samples express MAP2 compared to uninfected controls. TRPA1, M8, V1, and $Na_v1.7$ are present only in BN1 and BN2. GAPDH amplification in samples provides loading control, and GAPDH used in the absence reverse transciptase (–RT) controls for contaminating genomic DNA. (d) Representative calcium responses for 10 µM capsaicin (Cap), 100 µM Menthol (Men), and 100 µM mustard oil (MO). Calcium transients were measured using Map2::GCAMP5.G. Calcium responses were calculated as the change in fluorescence ($\Delta F$) over the initial fluorescence ($F_o$). Depolarization with 2.5 mM KCl was used at the beginning and end of each experiment to confirm neural identity and sustained functional capacity. (e) $\Delta F/F_o$ intensity plot showing the response of individual cells to each ligand. Each cell is represented in each column. Cells respond to KCl only (black circle), KCl plus one other ligand (the other circles), or KCl plus two other ligands (triangle or square). (f) Distribution of KCl responders that responded to either KCl only, KCl plus one other ligand, or KCl with two other ligands. Bars represent means from seven experiments. Error bars represent SEM. (g) Representative calcium responses for 100 µM Histamine (Hist), 100 µM Chloroquine (CQ), 10 µM BAM8-22 (BAM), 10 µM SLI-GRL (SLI). (h) $\Delta F/F_o$ intensity plots of three separate ligand combination regimes showing the response of individual cells to each ligand. Each cell is represented in each column. Cells respond to KCl only (black circle), KCl plus one other ligand (the other circles), or KCl plus two other ligands (triangles or squares). (i) Distribution of KCl responders in BN2 that responded to either KCl only, KCl plus one other ligand, or KCl with multiple ligands. Bars represent means from at least 2 experiments. Error bars represent SEM.

Figure 8:
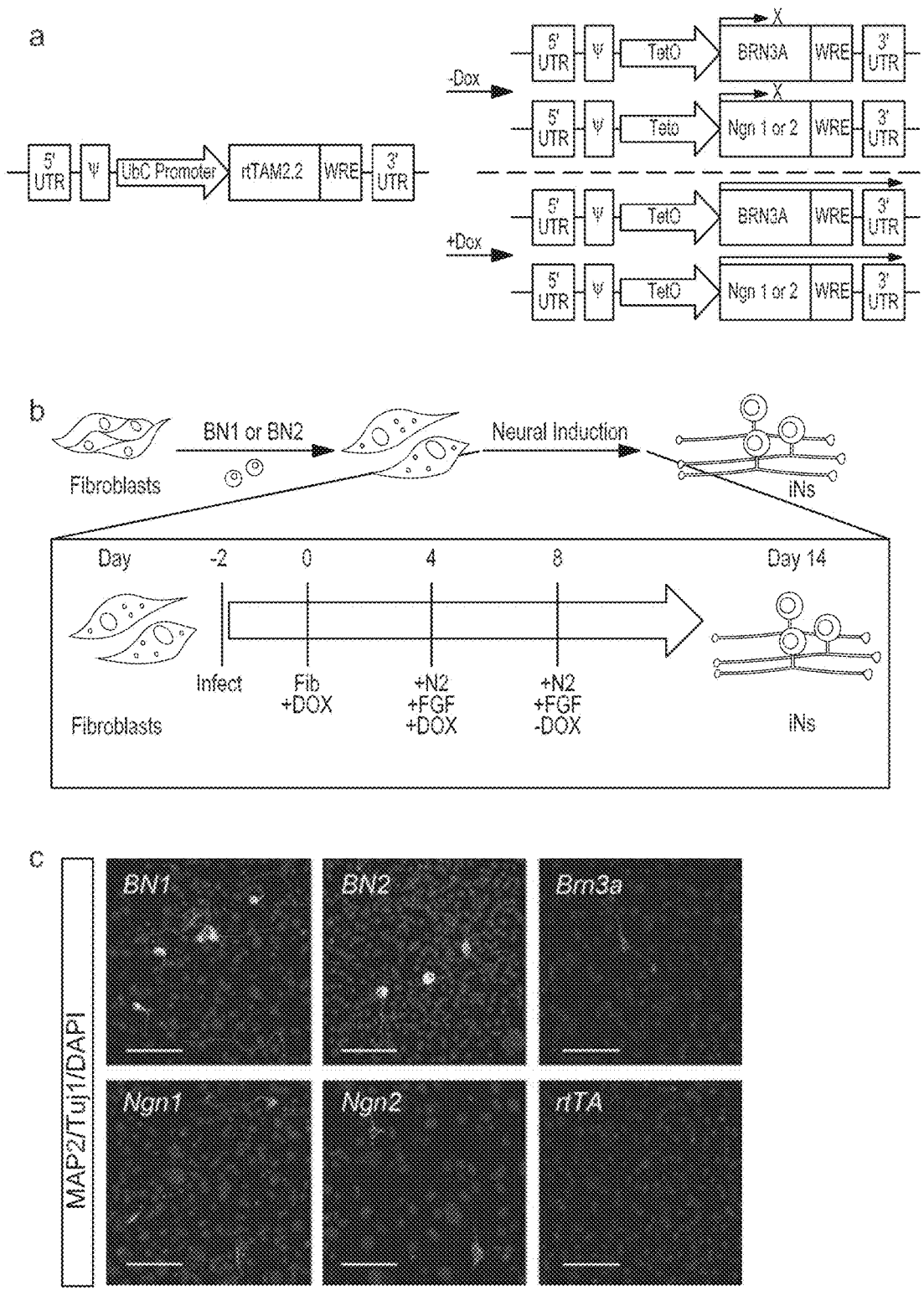

FIGS. 8A-8C show that ectopic expression of BN1 or BN1 mediates neural reprogramming. (a) Doxycycline inducible lentiviral vectors (b) Neural induction methods. (c) Representative staining for single and double ectopic expression of BN1 and BN1 in MEFs using protocol described in S1a.

Figure 9:
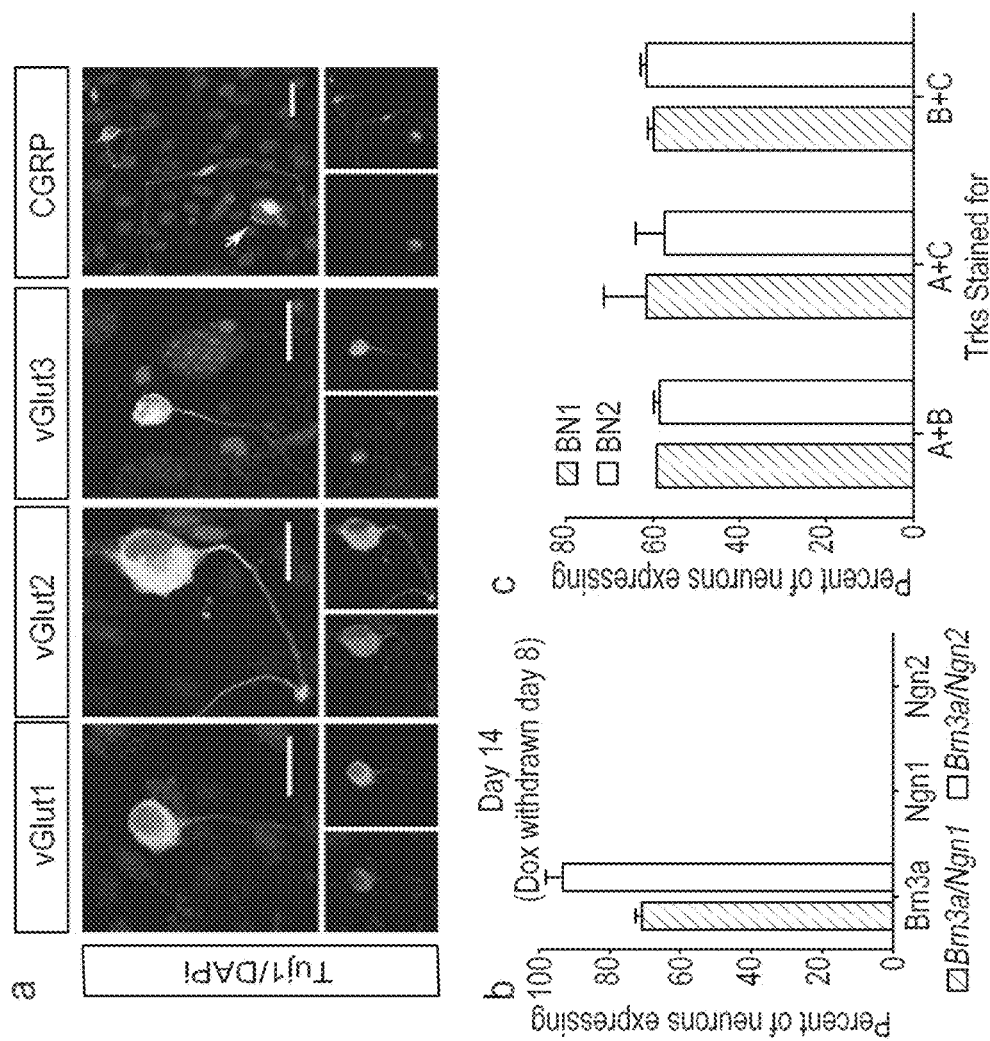

FIGS. 9A-9C show that BN1 and BN2 neurons possess molecular signatures of sensory neurons. (a) iSNs induced with either BN1 or BN2 are excitatory neurons show immunostaining for vGlut1, vGlut2, and vGlut3, CGRP in Tuj1 positive cells. Scale bars represent 25 µM. (b) Brn3a but not Ngn1/2 expression persists following dox withdrawal. (c) Quantification of neurons positive for each of the three Trk receptors individually and in pair wise combination. Bars represent means and error bars represent SEM from two independent experiments in which a minimum of 100 cells was counted.

Figure 10:
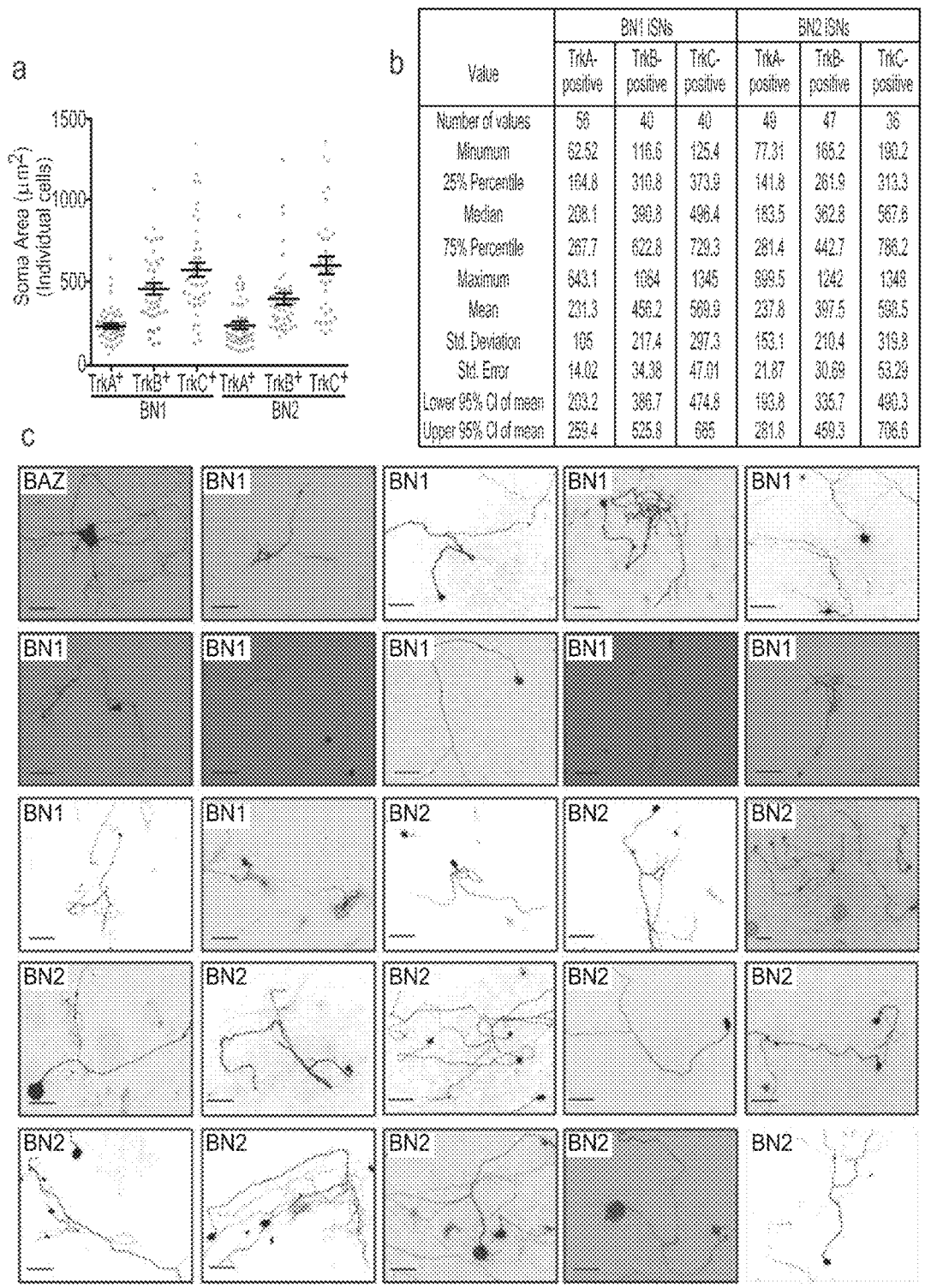

FIGS. 10A-10C show analysis of iSN morphologies. (a) TrkA, TrkB, and TrkC neurons have distinct distribution of soma size. Scatter plot of soma areas by Trk receptor immune-reactivity. (b) Table present statistical attributes of soma size distribution. Representative images of neurons induced with Brn2, Ascl1 (also called Mash1) and Zic1 (BAZ) and BN1 and BN2. Black is Tuj1 staining. Scale bar 100 µm. (c) representative neurite branching for iSNs generated with Brn2, Ascii, Zic1 (BAZ) or BN1 and BN2. Neurons were immunostained for Tuj1.

DETAILED DESCRIPTION

I. Overview

The present invention is predicated in part on the findings by the present inventors of transcription factors that convert mouse and human fibroblasts into sensory neurons. As detailed herein, it was found that two lineage-relevant transcription factors, without additional exogenous cues, can induce neurons that phenocopy many defining signatures of somatosensory neurons including morphological features, gene expression, and functional properties. The induced sensory neurons (iSNs) in mouse exhibit two key morphological hallmarks of peripheral sensory neurons, pseudounipolar morphology, and lineage-restricted size distributions. Specifically, it was found that neural reprograming with co-expression of the transcription factors, Brn3a/Ngn1 (BN1) or Brn3a/Ngn2 (BN2), is highly selective with the overwhelming majority of induced neurons assuming one of three major somatosensory neural lineages and express a specific combinatorial array of markers unique to somatosensory neurons. Also, no differences were observed between iSNs generated via Nng1 or Ngn2. Furthermore, the inventors were able to recapitulate these induced sensory neurons in human fibroblasts, and these iSNs possess the functional 'gold-standard' of nociceptive neurons, the ability to sense and selectively respond to noxious and itch inducing stimuli. These findings indicate that the iSNs are functional phenocopies of peripheral sensory neurons, and as a result are useful in the study of sensory biology, diseases, and drug screening directly in cells derived from humans of diverse genetic backgrounds.

While the observed iSNs are divided into three distinct somatosensory lineages that developmentally arise from common precursors, iSN conversion does not require transiting through a proliferative neural precursor. The direct conversion offers some clear advantages to generating in vitro neuronal models through directed differentiation from pluri- or multi-potent stem cells. For example, direct iSN conversion is rapid, efficient, and requires minimal manipulation of the culture environment. Furthermore, avoiding proliferative precursors via direct conversion limits opportunities for epigenetic changes that could deprogram pathogenic or phenotypically desired traits.

In accordance with these studies, the invention provides methods for generating induced sensory neurons from non-neuronal cells via co-expressing a combination of the Brn3a/Ngn1 (BN1) genes or the Brn3a/Ngn2 (BN2) genes. The methods establish a novel and elegant technique for directly inducing a unique neuronal sub-type from non-neuronal cells such as fibroblasts. Also encompassed by the invention are non-neuronal cells containing expressing vector(s) for transiently expressing the BN1 or BN2 genes, induced sensory neurons thus generated, as well as transgenic non-human animals harboring such non-neuronal cells or induced sensory neurons. By utilizing a minimal set of transcription factors, the methods provide a foundation for understanding how neural induction proceeds and a platform to screen for additional factors that enable selective induction of specific sensory sub-populations. Thus, the invention additionally provides methods for identifying other agents or cellular modulations that can improve the efficiency, accuracy or specificity of iSN induction, including transcription factors, miRNA, or other genetic and epigenetic modulations. Further provided in the invention are methods of employing iSNs generated in accordance with the invention in various therapeutic applications. The following sections provide guidance for making and using the compositions of the invention, and for carrying out the methods of the invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press (1$^{st}$ ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons (3$^{rd}$ ed., 2002); *Dictionary of Chemistry*, Hunt (Ed.), Routledge (1$^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press (4$^{th}$ ed., 2000). In addition, the following definitions are provided to assist the reader in the practice of the invention.

The term "agent" or "test agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved traits (such as higher binding affinity for a target molecule) is an approach that is well known in pharmaceutical chemistry.

As used herein, "contacting" has its normal meaning and refers to combining two or more agents (e.g., polypeptides or small molecule compounds) or combining agents and cells. Contacting can occur in vitro, e.g., combining two or more agents or combining a test agent and a cell or a cell lysate in a test tube or other container. Contacting can also occur in a cell or in situ, e.g., contacting two polypeptides in a cell by coexpression in the cell of recombinant polynucleotides encoding the two polypeptides, or in a cell lysate.

Stem cells are cells characterized by the ability of self-renewal through mitotic cell division and the potential to differentiate into a tissue or an organ. Embryonic stem cells (ESCs) are pluripotent stem cells derived from the inner cell mass of a blastocyst, an early-stage embryo. ESCs are pluripotent, that is, they are able to differentiate into all derivatives of the three primary germ layers: ectoderm, endoderm, and mesoderm. These include each of the more than 220 cell types in the adult body. Pluripotency distinguishes embryonic stem cells from adult stem cells found in adults; while embryonic stem cells can generate all cell types in the body, adult stem cells are multipotent and can produce only a limited number of cell types. Additionally, under defined conditions, embryonic stem cells are capable of propagating themselves indefinitely. This allows embryonic stem cells to be employed as useful tools for both research and regenerative medicine, because they can produce limitless numbers of themselves for continued research or clinical use.

Induced pluripotent stem cells (iPSCs) are a type of pluripotent stem cell artificially derived from a non-pluripotent cell—typically an adult somatic cell—by inducing a "forced" expression of specific genes. Induced pluripotent stem cells are similar to natural pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability, but the full extent of their relation to natural pluripotent stem cells is still being assessed. Induced pluripotent cells have been made from adult stomach, liver, skin cells, blood cells, prostate cells and urinary tract cells.

Sensory neurons are neurons responsible for converting various external stimuli that arise from the environment of an organism, producing corresponding internal stimuli. They are activated by sensory input, and send projections to other elements of the nervous system, ultimately conveying sensory information to the brain or spinal cord. Unlike neurons of the central nervous system, whose inputs come from other neurons, sensory neurons are activated by physical modalities such as visible light, sound, heat, physical contact, etc., or by chemical signals for example in the case of smell or taste. Peripheral sensory neurons are composed of three major lineages, nociceptors, mechanoceptors, and proprioceptors, which are demarcated by expression of TrkA, TrkB and TrkC, respectively. Peripheral sensory neurons arise from two waves of development coordinated by co-expression of Neurogenin 1 (Ngn1) and Neurogenin 2 (Ngn2).

Induced sensory neurons (iSNs) refer to cells of the neuronal lineage, i.e. mitotic neuronal progenitor cells and post-mitotic neuronal precursor cells and mature neurons, that arise from a non-neuronal cell by experimental manipulation. iSNs express markers specific for cells of the neuronal lineage, e.g. Tau, Tuj1, MAP2, NeuN, and the like, and may have characteristics of functional neurons, that is, they may be able to be depolarized, i.e., propagate an action potential, and they may be able to make and maintain synapses with other neurons.

miRNA (or microRNA) refers to a class of small RNA molecules that are capable of modulating RNA translation (see, Zeng and Cullen, RNA, 9:112-123, 2003; Kidner and Martienssen, Trends Genet, 19:13-6, 2003; Dennis et al., Nature, 420:732, 2002; and Couzinet al., Science 298:2296-7, 2002). MicroRNAs (miRNAs) encompass a family of ~22 nucleotide (nt) non-coding RNAs. These RNAs have been identified in organisms ranging from nematodes to humans. Many miRNAs are evolutionarily conserved widely across phyla, regulating gene expression by post-transcriptional gene repression. The long primary transcripts (pri-miRNAs) are transcribed by RNA polymerase II; processed by a nuclear enzyme Drosha; and released as a ~60 bp hairpin precursor (pre-miRNAs). Pre-miRNAs are processed by RNase III enzymes, Dicer, to ~22 nt (mature miRNAs) and then incorporated into RISC (RNA-induced silencing complex). The complex of miRNAs-RISC binds the 3' UTR of the target mRNAs and conducts translational repression or degradation of mRNAs.

The term "modulate" with respect to a reference molecule or cellular activity (e.g., transcription or DNA methylation) refers to inhibition or activation of a biological activity of the reference molecule or cellular activity. Modulation can be up-regulation (i.e., activation or stimulation) or down-regulation (i.e., inhibition or suppression). The mode of action can be direct, e.g., through binding to the reference molecule. The modulation can also be indirect, e.g., through binding to and/or modifying another molecule which otherwise modulates the reference molecule.

Enhanced efficiency of conversion refers to an up-regulated ability of a culture of non-neuronal cells to give rise to the induced sensory neurons when contacted with a compound (or subjected to a genetic or epigenetic modulation) relative to a culture of the same type of cells that is not contacted with the compound (or subjected to the modulation). By enhanced, it is meant that the cell cultures have an ability to give rise to induced sensory neurons that is greater than the ability of a population that is not contacted with the candidate agent or induction agent, e.g., 150%, 200%, 300%, 400%, 600%, 800%, 1000%, or 2000% of the ability of the uncontacted (or unmodulated) population. In other words, the cell cultures produce 1.5-fold or more, 2-fold or more, 3-fold or more, 4-fold or more, 6-fold or more, 8-fold or more, 10-fold or more, 20-fold or more, 30-fold or more, 50-fold or more, 100-fold or more, 200-fold or more the number of induced sensory neurons as the uncontacted (or unmodulated) population.

"Polynucleotide" or "nucleic acid sequence" refers to a polymeric form of nucleotides (polyribonucleotide or polydeoxyribonucleotide). In some instances a polynucleotide refers to a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. Polynucleotides can be ribonucleotides, deoxyribonucleotides, or modified forms of either nucleotide.

A polypeptide or protein refers to a polymer in which the monomers are amino acid residues that are joined together through amide bonds. When the amino acids are alpha-amino acids, either the L-optical isomer or the D-optical isomer can be used, the L-isomers being typical. A polypeptide or protein fragment can have the same or substantially identical amino acid sequence as the naturally occurring protein. A polypeptide or peptide having substantially identical sequence means that an amino acid sequence is largely, but not entirely, the same, but retains a functional activity of the sequence to which it is related.

Polypeptides may be substantially related due to conservative substitutions. A conservative variation denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. Other illustrative examples of conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine.

The term "subject" includes mammals, especially humans, as well as other non-human animals, e.g., horse, dogs and cats.

A "substantially identical" nucleic acid or amino acid sequence refers to a polynucleotide or amino acid sequence which comprises a sequence that has at least 75%, 80% or 90% sequence identity to a reference sequence as measured by one of the well-known programs described herein (e.g., BLAST) using standard parameters. The sequence identity is preferably at least 95%, more preferably at least 98%, and most preferably at least 99%. In some embodiments, the subject sequence is of about the same length as compared to the reference sequence, i.e., consisting of about the same number of contiguous amino acid residues (for polypeptide sequences) or nucleotide residues (for polynucleotide sequences).

Sequence identity can be readily determined with various methods known in the art. For example, the BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)). Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein, "treating" or "ameliorating" includes (i) preventing a pathologic condition (e.g., sensory neuronopathy) from occurring (e.g. prophylaxis); (ii) inhibiting the pathologic condition (e.g., sensory neuronopathy) or arresting its development; and (iii) relieving symptoms associated with the pathologic condition (e.g., sensory neuronopathy). Thus, "treatment" includes the administration of an isolated (and/or purified) iSN population of the invention and/or other therapeutic compositions or agents to prevent or delay the onset of the symptoms, complications, or biochemical indicia of a disease described herein, alleviating or ameliorating the symptoms or arresting or inhibiting further development of the disease, condition, or disorder. "Treatment" further refers to any indicia of success in the treatment or amelioration or prevention of the disease, condition, or disorder described herein, including any objective or subjective parameter such as abatement; remission; diminishing of symptoms or making the disease condition more tolerable to the patient; slowing in the rate of degeneration or decline; or making the final point of degeneration less debilitating. Detailed procedures for the treatment or amelioration of the disorder or symptoms thereof can be based on objective or subjective parameters, including the results of an examination by a physician.

A "variant" of a reference molecule (e.g., a Neurogenin 1 or Neurogenin 2) is meant to refer to a molecule substantially similar in structure and biological activity to either the entire reference molecule, or to a fragment thereof. Thus, provided that two molecules possess a similar activity, they are considered variants as that term is used herein even if the composition or secondary, tertiary, or quaternary structure of one of the molecules is not identical to that found in the other, or if the sequence of amino acid residues is not identical.

A "vector" is a replicon, such as plasmid, phage or cosmid, to which another polynucleotide segment may be attached so as to bring about the replication of the attached segment. Vectors capable of directing the expression of genes encoding for one or more polypeptides are referred to as "expression vectors".

A retrovirus (e.g., a lentivirus) based vector or retroviral vector means that genome of the vector comprises components from the virus as a backbone. The viral particle generated from the vector as a whole contains essential vector components compatible with the RNA genome, including reverse transcription and integration systems. Usually these will include the gag and pol proteins derived from the virus. If the vector is derived from a lentivirus, the viral particles are capable of infecting and transducing non-dividing cells. Recombinant retroviral particles are able to deliver a selected exogenous gene or polynucleotide sequence such as therapeutically active genes, to the genome of a target cell.

III. Brn3a and Ngn1/Ngn2 Genes for Inducing Formation of Sensory Neurons

To generate induced sensory neurons (iSNs) from non-neuronal cells, methods of the invention entail co-expressing the Brn3a gene (genomic or cDNA sequence) and the Nng1 (or Ngn2) gene (genomic or cDNA sequence) in the non-neuronal cells. Brn3a (also called Pou4f1) encodes the brain-specific homeobox/POU domain protein 3A (BRN3A), aka "POU-domain transcription factor" (POU4F1), which regulates the transition from neurogenesis to mature terminally differentiated state. Neurogenins are a family of bHLH transcription factors involved in specifying neuronal differentiation. They are essential for the formation of dorsal root ganglia. Neurogenin 1 (Ngn1) acts as a regulator for neuronal differentiation by binding to enhancer regulatory elements on genes that encode transcriptional regulators of neurogenesis. Nng1 is a proneural gene because its expression is seen prior to neural lineage determination. In order for Nng1 to bind with high fidelity to genomic DNA, it must dimerize with another bHLH protein. Neurogenin 2 (Ngn2) is a transcription factor involved in both neurogenesis and neural specification. This protein binds to enhancer box regulatory elements on the promoters of many genes related to neurogenesis and neural specification. For sufficient DNA binding, Ngn2 must form a dimer with an enhancer protein.

Brn3a gene and Ngn1/Ngn2 genes from various species can be readily employed in the practice of the present invention. Genomic and cDNA sequences of these genes are all known in the art. See, e.g., Trieu et al., Development 130, 111-121, 2003; Lanier et al., Dev. Dyn. 238, 3065-3079, 2009; Velkey et al., Dev. Dyn. 242, 230-253, 2013; and Ma et al., Genes Dev. 13:1717-28, 1999. For example, Brn3a genomic and/or cDNA sequences from various species have been reported, cloned, and characterized in the literature, including human Brn3a gene, mouse Brn3a gene, rat Brn3a gene, chicken Brn3a gene, and zebrafish Brn3a gene. See e.g., He et al., Nature 340, 35-41, 1989; Collum et al., Nucleic Acids Res. 20, 4919-4925, 1992; Gerrero et al., Proc. Natl. Acad. Sci. U.S.A. 90, 10841-10845, 1993; Bhargava et al., Proc. Natl. Acad. Sci. U.S.A. 90, 10260-10264, 1993; Turner et al., Neuron 12, 205-218, 1994; Xiang et al., J. Neurosci. 15, 4762-4785, 1995; Smith et al., J. Biol. Chem. 272, 1382-1388, 1997; Fedtsova and Turner, Mech. Dev. 105, 129-144, 2001; Thomas et al., Biochem. Biophys. Res. Commun. 318, 1045-1051, 2004; Aizawa et al., Curr Biol. 15, 238-43, 2005; and Trieu et al., Development 130, 111-121, 2003. Similarly, Nng1 and Ngn2 cDNA sequences from human, mouse, rat, chicken, xenopus, zebrafish, and many other species have also been cloned and functionally characterized. See, e.g., Sommer et al., Mol. Cell. Neurosci. 8, 221-241, 1996; McCormick et al., Mol. Cell. Biol. 16, 5792-5800, 1996; Ma et al., Cell 87, 43-52, 1996; Gradwohl et al., Dev., Biol. 180, 227-241, 1996; Tamimi et al., Genomics 40, 355-357, 1997; Fode et al., Neuron 20, 483-494, 1998; Korzh et al., Dev. Dyn. 213, 92-104, 1998; Ma et al., Genes Dev. 13:1717-28, 1999; Perez et al., Development 126, 1715-1728, 1999; Franklin et al., J. Child Neurol. 16, 849-853, 2001; Simons et al., Dev. Biol. 229, 327-339, 2001; Kim et al., Exp. Mol. Med. 34, 469-475, 2002; Klein et al., Dev. Dyn. 225, 384-391, 2002; and Zimin et al., Genome Biol. 10, R42, 2009. The specific genomic or mRNA sequences corresponding to these genes are also available from, e.g., GenBank. Any of these Brn3a genes and Ngn1/Ngn2 genes can be employed in the practice of the present invention.

In addition to the various wildtype Brn3a genes (or cDNA sequences) and Ngn1/Ngn2 genes (or cDNA sequences) described above, variants or functional derivatives of such genes (or cDNA sequences) can also be used in the invention. Thus, methods of the invention can utilize a variant or modified Brn3a sequence and/or Nng1 (or Ngn2) sequence that is substantially identical to its wildtype counterpart, e.g., conservatively modified variants. For example, the substantially identical variants should contain a sequence that is at least 80%, 90%, 95% or 99% identical to the wildtype sequence. In some embodiments, the functional derivatives are variants produced by non-conservative substitutions to the extent that that they substantially retain the activities of the native proteins. Modification to a polynucleotide encoding a polypeptide of interest can be performed with standard techniques routinely practiced in the art. In some other embodiments, the functional derivatives can contain a partial sequence of the wildtype Brn3a gene and/or the Ngn1 (or Ngn2) gene. Such partial sequence should encode a functionally fragment that possesses some or all of the cellular functions of the wildtype protein, e.g., activities in regulating neurogenesis. Cellular functions (e.g., transcriptional regulation) of the BRN3A, Nng1 and Ngn2 transcription factors have been delineated in the art. Based on their structural and functional information known in the art, cloning and expression of functional fragments of these transcription factors can be readily carried out via standard techniques of molecular biology. In addition, the functional derivatives of BRN3A, Nng1 and Ngn2 described herein can be subject to the screening methods described below to confirm their activities in promoting formation of induced sensory neurons.

IV. Non-Neuronal Cells for Generating Induced Sensory Neurons

Various non-neuronal cells can be employed in the present invention for generating induced sensory neurons. These include fibroblasts, stem cells, blood cells, and other non-neuronal somatic cells. The non-neuronal cells can be obtained from both human and non-human animals including vertebrates and mammals. Thus, other than human cells and mouse cells as exemplified herein, the cells can also be from other animal species such as bovine, ovine, porcine, canine, feline, avian, bony and cartilaginous fish, rats, other primates including monkeys, as well as other animals such as ferrets, sheep, rabbits and guinea pigs.

In general, non-neuronal cells suitable for the methods of the invention can be any somatic cells that would not give rise to a sensory neuron in the absence of experimental manipulation. Examples of such non-neuronal somatic cells include differentiating or differentiated cells from ectodermal (e.g., keratinocytes), mesodermal (e.g., fibroblast), endoderm (e.g., pancreatic cells), or neural crest lineages (e.g., melanocytes). The somatic cells may be, for example, pancreatic beta cells, glial cells (e.g., oligodendrocytes, astrocytes), hepatocytes, hepatic stem cells, cardiomyocytes, skeletal muscle cells, smooth muscle cells, hematopoietic cells, osteoclasts, osteoblasts, pericytes, vascular endothelial cells, schwann cells, dermal fibroblasts, and the like. They may be terminally differentiated cells, or they may be capable of giving rise to cells of a specific, non-neuronal lineage, e.g., cardiac stem cells, hepatic stem cells, and the like. The somatic cells are readily identifiable as non-neuronal by the absence of neuronal-specific markers that are well-known in the art, as described herein. Of interest are cells that are vertebrate cells, e.g., mammalian cells, such as human cells, including adult human cells.

Some preferred embodiments of the invention utilize fibroblasts to generate iSNs. As exemplified herein, these include both embryonic fibroblasts and adult fibroblasts. The fibroblasts can be obtained or derived from various animal (e.g., mammal) species, e.g., human, mouse and rat. In some embodiments, stem cells can be used for conversion into iSNs. Stem cells suitable for practicing the invention include and are not limited to hematopoietic stem cells (HSC), embryonic stem cells, mesenchymal stem cells, and also induced pluripotent stem cells (iPSCs). Still some embodiments of the invention can utilize somatic cells other than fibroblasts such as blood cells. In these embodiments, blood cells obtained from various organs including, e.g., liver, spleen, bone marrow and the lymphatic system, may all be employed in the practice of the invention. In addition, methods of the invention may also be used for generating iSNs from peripheral blood cells such as erythrocytes, leukocytes and thrombocytes. In some other embodiments, the employed non-neuronal somatic cells can be glial cells (glia). Glia or glial cells refer to non-neuronal cells found in close contact with neurons, and encompass a number of different cells, including but not limited to the microglia, macroglia, neuroglia, astrocytes, astroglia, oligodendrocytes, ependymal cells, radial glia, Schwann cells, satellite cells, and enteric glial cells.

V. Expressing Brn3a and Ngn1/Ngn2 in Non-Neuronal Cells

Co-expressing Brn3a/Ngn1 (BN1) genes, Brn3a/Ngn2 (BN2) genes, or their functional variants described above in a non-neuronal cell can be carried out in accordance with the methods exemplified herein and other methods well known in the art. Preferably, the genes are transiently expressed in the non-neuronal cell. This can be accomplished via cloning the genes (genomic or cDNA sequences) into expression vector(s) and then introducing the expression vector(s) into the target non-neuronal cells. The two genes can be co-expressed from the same vector, as exemplified herein. Alternatively, the two genes can be cloned into and expressed separately from two expression vectors. Preferably, the genes are cloned into retroviruses or retroviral vectors (lentiviral vectors) for transducing into the non-neuronal cells. As demonstrated in the Examples below, a recombinant retroviral vector expressing the BN1 genes or the BN2 genes can be readily constructed by inserting the genes operably into the vector, replicating the vector in an appropriate packaging cell as described herein, obtaining viral particles produced therefrom, and then infecting target non-neuronal cells (e.g., fibroblasts) with the recombinant viruses.

Cloning the BN1 or BN2 genes into expression vectors and expressing the genes in non-neuronal cells can be performed using the specific protocols described herein and methods routinely practiced in the art, e.g., as described in Sambrook et al., *Molecular Cloning: A Laboratory Manual*, Cold Spring Harbor Press, N.Y., (3$^{rd}$ ed., 2000); and Brent et al., *Current Protocols in Molecular Biology*, John Wiley & Sons, Inc. (ringbou ed., 2003). Detailed procedures for cloning genes of interest into lentiviral vectors, producing lentiviral viruses in packaging cells (e.g., 293T cells), and infecting host cells with the viruses for expression of the genes are also described in the art, e.g., Boland et al. Nature 461, 91-94, 2009. Unless otherwise stated, other procedures or steps required for practicing the present invention can be based on standard procedures as described, e.g., in Murray et al., *Gene Transfer and Expression Protocols*, The Humana Press Inc. (1991); Davis et al., *Basic Methods in Molecular Biology*, Elsevier Science Publishing, Inc., New York, USA (1986); or *Methods in Enzymology: Guide to Molecular Cloning Techniques* Vol. 152, S. L. Berger and A. R. Kimmerl Eds., Academic Press Inc., San Diego, USA (1987); *Current Protocols in Protein Science* (CPPS) (John E. Coligan, et. al., ed., John Wiley and Sons, Inc.), *Current*

*Protocols in Cell Biology* (CPCB) (Juan S. Bonifacino et. al. ed., John Wiley and Sons, Inc.), and *Culture of Animal Cells: A Manual of Basic Technique* by R. Ian Freshney, Publisher: Wiley-Liss; 5th edition (2005), *Animal Cell Culture Methods* (Methods in Cell Biology, Vol. 57, Jennie P. Mather and David Barnes editors, Academic Press, 1st edition, 1998).

In some embodiments, expression of the BN1 or BN2 genes in the non-neuronal cells is controlled temporally. Temporal expression of these genes can be achieved via, e.g., the use of an inducible expression system. Any inducible expression method can be employed in the practice of the present invention. For example, the expression vectors can incorporate an inducible promoter that is active under environmental or developmental regulation, e.g., doxycycline (dox)-inducible lentiviral vectors. As exemplified herein, the genes can be expressed under the control of a promoter that is activated when bound by a reverse tetracycline transactivator (rtTA) and contacted by doxycycline, tetracycline, or a tetracycline analog. The tTA protein is created by fusing one protein, TetR (tetracycline repressor), found in Escherichia coli bacteria, with the activation domain of another protein, VP16, found in the Herpes Simplex Virus. The resulting tTA protein is able to bind to DNA at specific TetO operator sequences. In the inducible expression system, several repeats of the TetO sequences are placed upstream of a minimal promoter such as the CMV promoter. The entirety of several TetO sequences with a minimal promoter is called a tetracycline response element (TRE), because it responds to binding of the tetracycline transactivator protein tTA by increased expression of the gene or genes downstream of its promoter. Typically, in addition to the expression vector(s) under the control of TetO for expressing the intended exogenous genes (e.g., the BN1 or BN2 genes), another vector for expressing a reverse tet transactivator is included in the inducible expression system.

The inducible expression system allows optimization of expression of the BN1 or BN2 genes in the non-neuronal cells that are appropriate the neurons to mature. The inducible expression system may also allow for higher and/or more prolonged expression of the genes compared to non-inducible expression systems. In some preferred embodiments of the invention, induction of the BN1 or BN2 gene expression can last for at least about 2 days, 4 days, 8 days, 12 days, e.g., between 2-8, 4-10, 6-12, 8-14, 10-20, 12-30, or 15-40 days. The period of induction refers to the period from initial expression of the BN1 or BN2 genes (or induction of expression with addition of doxycycline as exemplified herein) to the time the iSNs are selected (or termination of induction with doxycycline). Following introduction of the expression vectors under the control of TetO, expression of the BN1 or BN2 genes can be induced in the non0neuronal cells with tetracycline, doxycycline, or another tetracycline analog, and the cells can be cultured and selected for iSNs. Detailed protocols for inducible expression of exogenous genes in a host cell, e.g., using the rtTA/TetO system exemplified herein, are well known in the art (e.g., WO 2011005580).

Retroviruses are a group of single-stranded RNA viruses characterized by an ability to convert their RNA to double-stranded DNA in infected cells by a process of reverse-transcription. The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These elements contain strong promoter and enhancer sequences and are also required for integration in the host cell genome.

Retroviral vectors or recombinant retroviruses are widely employed in gene transfer in various therapeutic or industrial applications. For example, gene therapy procedures have been used to correct acquired and inherited genetic defects, and to treat cancer or viral infection in a number of contexts. The ability to express artificial genes in humans facilitates the prevention and/or cure of many important human diseases, including many diseases which are not amenable to treatment by other therapies. For a review of gene therapy procedures, see Anderson, *Science* 256:808-813, 1992; Nabel & Feigner, TIBTECH 11:211-217, 1993; Mitani & Caskey, TIBTECH 11:162-166, 1993; Mulligan, *Science* 926-932, 1993; Dillon, TIBTECH 11:167-175, 1993; Miller, *Nature* 357:455-460, 1992; Van Brunt, *Biotechnology* 6:1149-1154, 1998; Vigne, *Restorative Neurology and Neuroscience* 8:35-36, 1995; Kremer & Perricaudet, *British Medical Bulletin* 51:31-44, 1995; Haddada et al., in *Current Topics in Microbiology and Immunology* (Doerfler & Böhm eds., 1995); and Yu et al., *Gene Therapy* 1:13-26, 1994.

To construct retroviral vectors for transient expression of the BN1 or BN2 genes, a polynucleotide encoding one or both of the genes is inserted into the viral genome in the place of certain viral sequences to produce a viral construct that is replication-defective. In order to produce virions, a producer host cell or packaging cell line is employed. The host cell usually expresses the gag, pol, and env genes but without the LTR and packaging components. When the recombinant viral vector containing the gene of interest together with the retroviral LTR and packaging sequences is introduced into this cell line (e.g., by calcium phosphate precipitation), the packaging sequences allow the RNA transcript of the recombinant vector to be packaged into viral particles, which are then secreted into the culture media. The media containing the recombinant retroviruses is then collected, optionally concentrated, and used for transducing host cells (e.g., fibroblasts or stem cells) in gene transfer applications.

Suitable host or producer cells for producing recombinant retroviruses or retroviral vectors according to the invention are well known in the art (e.g., 293T cells exemplified herein). Many retroviruses have already been split into replication defective genomes and packaging components. For other retroviruses, vectors and corresponding packaging cell lines can be generated with methods routinely practiced in the art. The producer cell typically encodes the viral components not encoded by the vector genome such as the gag, pol and env proteins. The gag, pol and env genes may be introduced into the producer cell and stably integrated into the cell genome to create a packaging cell line. The retroviral vector genome is then introduced-into the packaging cell line by transfection or transduction to create a stable cell line that has all of the DNA sequences required to produce a retroviral vector particle. Another approach is to introduce the different DNA sequences that are required to produce a retroviral vector particle, e.g. the env coding sequence, the gag-pol coding sequence and the defective retroviral genome into the cell simultaneously by transient triple transfection. Alternatively, both the structural components and the vector genome can all be encoded by DNA stably integrated into a host cell genome.

The methods of the invention can be practiced with various retroviral vectors and packaging cell lines well known in the art. Widely used retroviral vectors include those based upon murine leukemia virus (MuLV), gibbon ape leukemia virus (GaLV), simian immunodeficiency virus (SIV), human immunodeficiency virus (HIV), and combinations thereof (see, e.g., Buchscher et al., *J. Virol.* 66:2731-2739, 1992; Johann et al., *J. Virol.* 66:1635-1640, 1992; Sommerfelt et al., *Virol.* 176:58-59, 1990; Wilson et al., *J. Virol.* 63:2374-2378, 1989; Miller et al., *J. Virol.* 65:2220-2224, 1991; and PCT/US94/05700). Particularly suitable for the present invention are lentiviral vectors. Lentiviral vectors are retroviral vector that are able to transducer or infect non-dividing cells and typically produce high viral titers. Lentiviral vectors have been employed in gene therapy for a number of diseases. For example, hematopoietic gene therapies using lentiviral vectors or gamma retroviral vectors have been used for x-linked adrenoleukodystrophy and beta thalassaemia. See, e.g., Kohn et al., Clin. Immunol. 135:247-54, 2010; Cartier et al., Methods Enzymol. 507: 187-198, 2012; and Cavazzana-Calvo et al., Nature 467: 318-322, 2010. Methods of the invention can be readily applied in gene therapy or gene transfer with such vectors. In some other embodiments, other retroviral vectors can be used in the practice of the methods of the invention. These include, e.g., vectors based on human foamy virus (HFV) or other viruses in the Spumavirus genera.

In particular, a number of viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent. pLASN and MFG-S are examples are retroviral vectors that have been used in clinical trials (Dunbar et al., *Blood* 85:3048-305 (1995); Kohn et al., *Nat. Med.* 1:1017-102 (1995); Malech et al., *Proc. Natl. Acad. Sci. U.S.A.* 94:22 12133-12138 (1997)). PA317/pLASN was the first therapeutic vector used in a gene therapy trial (Blaese et al., *Science* 270:475-480, 1995). Transduction efficiencies of 50% or greater have been observed for MFG-S packaged vectors (Ellem et al., *Immunol Immunother.* 44:10-20, 1997; Dranoff et al., *Hum. Gene Ther.* 1:111-2, 1997). Many producer cell line or packaging cell line for transfecting retroviral vectors and producing viral particles are also known in the art. The producer cell to be used in the invention needs not to be derived from the same species as that of the target cell (e.g., human target cell). Instead, producer or packaging cell lines suitable for the present invention include cell lines derived from human (e.g., HEK 293 cell or 293T cell), monkey (e.g., COS-1 cell), mouse (e.g., NIH 3T3 cell) or other species (e.g., canine). Some of the cell lines are disclosed in the Examples below. Additional examples of retroviral vectors and compatible packaging cell lines for producing recombinant retroviruses in gene transfers are reported in, e.g., Markowitz et al., Virol. 167:400-6, 1988; Meyers et al., Arch. Virol. 119:257-64, 1991 (for spleen necrosis virus (SNV)-based vectors such as vSNO21); Davis et al., Hum. Gene. Ther. 8:1459-67, 1997 (the "293-SPA" cell line); Povey et al., Blood 92:4080-9, 1998 (the "1MI-SCF" cell line); Bauer et al., Biol. Blood Marrow Transplant. 4:119-27, 1998 (canine packaging cell line "DA"); Gerin et al., Hum. Gene Ther. 10:1965-74, 1999; Sehgal et al., Gene Ther. 6:1084-91, 1999; Gerin et al., Biotechnol. Prog. 15:941-8, 1999; McTaggart et al., Biotechnol. Prog. 16:859-65, 2000; Reeves et al., Hum. Gene. Ther. 11:2093-103, 2000; Chan et al., Gene Ther. 8:697-703, 2001; Thaler et al., Mol. Ther. 4:273-9, 2001; Martinet et al., Eur. J. Surg. Oncol. 29:351-7, 2003; and Lemoine et al., I .Gene Med. 6:374-86, 2004. Any of these and other retroviral vectors and packaing producer cell lines can be used in the practice of the present invention.

Many of the retroviral vectors and packing cell lines used for gene transfer in the art can be obtained commercially. For example, a number of retroviral vectors and compatible packing cell lines are available from Clontech (Mountain View, Calif.). Examples of lentiviral based vectors include, e.g., pLVX-Puro, pLVX-IRES-Neo, pLVX-IRES-Hyg, and pLVX-IRES-Puro. Corresponding packaging cell lines are also available, e.g., Lenti-X 293T cell line. In addition to lentiviral based vectors and packaging system, other retroviral based vectors and packaging systems are also commercially available. These include MMLV based vectors pQCXIN, pQCXIQ and pQCXIH, and compatible producer cell lines such as HEK 293 based packaging cell lines GP2-293, EcoPack 2-293 and AmphoPack 293, as well as NIH/3T3-based packaging cell line RetroPack PT67. Any of these and other retroviral vectors and producer cell lines may be employed in the practice of the present invention.

VI. Therapeutic and Other Applications

Induced sensory neurons (iSNs) produced in accordance with the present invention can find various therapeutic and non-therapeutic applications. They can be used in cell replacement therapy to treat, ameliorate symptoms of, or prevent development of various diseases, e.g., neurological conditions or disorders that are associated with or mediated by a loss or degeneration of sensory neurons, as well as disorders that are associated with or caused by aberrantly functioning sensory neurons. In these applications, iSN cells prepared from non-neuronal cells of the subject in need of treatment can be transplanted or transferred to the same subject suffering from any of a wide range of diseases or disorders associated with or mediated by sensory neuron death or degeneration. The transplanted cells can reconstitute or supplement differentiating or differentiated sensory neurons in the subject. These therapeutic applications may be directed either to treating the cause of the disease or to treating the effects of the disease or condition. For example, therapy may be directed at replacing sensory neurons whose death or degeneration caused the disease, e.g., various sensory neuronopathies. The therapies can also be used in replacing sensory neurons that died as a result of the disease, e.g., ocular disorders such as age related macular degeneration (AMD).

Some embodiments of the invention are intended for treating sensory neuronopathies or sensory neuron diseases. Sensory neuronopathies encompass of a group of paraneoplastic, dysimmune, toxic, or idiopathic disorders or conditions that are characterized by degeneration of peripheral sensory neurons in dorsal root ganglia. Examples include paraneoplastic sensory neuronopathy, hereditary sensory and autonomic neuropathy, HIV infection, Sjögren's syndrome, various connective diseases, Freidreich's ataxia, and other rare idiopathic cases. See, e.g., Hainfellner et al., Ann. Neurol., 39:543-7, 1996; Kurokawa et al., J. Neurol. Neurosurg. Psychiatry 65: 278-9, 1998; Lodi et al., Antioxid. Redox Signal. 8: 438-43, 2006; and Colli et al., Surg Neurol., 69: 266-73, 2008. Sensory neuronopathies are frequently associated with life-threatening diseases such as cancer or potentially treatable diseases such as immune-mediated diseases. Sensory neuron diseases suitable for treatment with methods of the invention include sensory neuronopathies associated with immune-mediated and neoplastic diseases, and viral infections, and vitamin intoxication, and neurotoxic drugs. See, e.g., Horwich et al., Ann Neurol, 2: 7-19, 1977; Griffin et al., Ann Neurol, 27: 304-315, 1990; Merchut et al., Neurol., 43: 2410-2411, 1993; Scaravilli et al., Acta. Neuropathol. (Berl), 84: 163-170, 1992; Rubin et al., Muscle Nerve, 22: 1607-1610, 1999; Ramos et al., Rev Neurol, 28: 1067-1069, 1999; Shimazaki et al., J. Neurol Sci, 194: 55-58, 2002; Schaumburg et al., N Engl. J. Med, 309: 445-448, 1983; and Quasthoff et al., J. Neurol., 249: 9-17, 2002.

Some other embodiments of the invention are directed to treating ocular neovascularization or vascular degenerative disorders that are associated with or caused by problems and decay of vision related sensory neurons. The five basic classes of neurons within the retina are photoreceptor cells, bipolar cells, ganglion cells, horizontal cells, and amacrine cells. Examples of diseases or conditions associated with these sensory neurons include macular degeneration, degeneration of the central visual field due to either cellular debris or blood vessels accumulating between the retina and the choroid, thereby disturbing and/or destroying the complex interplay of neurons that are present there. Other examples include glaucoma, loss of retinal ganglion cells which causes some loss of vision to blindness, and diabetic retinopathy, which is related to poor blood sugar control due to diabetic damages of the tiny blood vessels in the retina. Additional ocular vascular disorder that may be treated with methods of the invention include ischemic retinopathy, iris neovascularization, intraocular neovascularization, corneal neovascularization, retinal neovascularization, choroidal neovascularization, diabetic retinal ischemia, and retinal degeneration.

The subjects suitable for treatment with methods of the invention can be neonatal, juvenile or fully mature adults. In some embodiments, the subjects to be treated are neonatal subjects suffering from a disease or disorder noted above. In some preferred embodiments, the subjects are human, and the iSN to be used in the treatment are human cells, preferably autologous cells isolated from the same subject to be treated. In the various therapeutic applications of the invention, an iSN population is typically first generated with non-neuronal cells (e.g., fibroblasts or glial cells) from the subject in need of treatment, using methods described herein. The iSN population can then be transferred to, or close to, an injured site in the subject. Alternatively, the cells can be introduced to the subject in a manner allowing the cells to migrate, or home, to the injured site. The transferred cells may advantageously replace the damaged or injured cells and allow improvement in the overall condition of the subject. In some instances, the transferred cells may stimulate tissue regeneration or repair. In some embodiments, the induced sensory neurons may be transplanted directly to an injured site to treat a sensory neuronopathy or neurological condition. The iSN replacement therapies can be performed with protocols well known in the art for cell transplantation. See, e.g., Morizane et al., Cell Tissue Res., 331(1):323-326, 2008; Coutts and Keirstead, Exp. Neurol., 209(2):368-377, 2008; and Goswami and Rao, Drugs, 10(10):713-719, 2007. Other techniques and specific procedures for carrying out the therapeutic methods of the invention can be based on or modified from methods well known in the art. See, e.g., Areman et al., Cellular Therapy: Principles, Methods, and Regulations, American Association of Blood Banks (AABB), 1$^{st}$ ed., 2009; Wingard et al., *Hematopoietic Stem Cell Transplantation: A Handbook for Clinicians*, American Association of Blood Banks (AABB); 1$^{st}$ ed., 2009; and Remington: *The Science and Practice of Pharmacy*, Mack Publishing Co., 20$^{th}$ ed., 2000.

In general, the number of iSN cells to be administered to the subject should be sufficient for arresting the disease state, e.g., at least about $1 \times 10^2$, at least about $1 \times 10^3$, at least about $1 \times 10^4$, at least $1 \times 10^5$, or at least $1 \times 10^6$ cells. The number of cells to be administered may depend upon the severity of the disease or condition, the age of the subject and other factors that will be readily apparent to one of ordinary skill in the art. The cells may be administered in a single dose or by multiple dose administration over a period of time, as may be determined by the physician in charge of the treatment. Also, the number of cells and frequency of administration can vary depending on whether the treatment is prophylactic or therapeutic. In prophylactic applications, a relatively low number of cells may be administered at relatively infrequent intervals over a long period of time. Some subjects may continue to receive treatment for the rest of their lives. In therapeutic applications, a relatively high number of cells at relatively short intervals may be required until progression of the disease is reduced or terminated, and preferably until the subject shows partial or complete amelioration of symptoms of the disease or disorder. Thereafter, the subject can be administered a prophylactic regime.

Other than therapeutic applications, iSNs generated with methods of the invention can be used as a basic research or drug discovery tool. Some embodiments of the invention are directed to identifying agents or modulations that can promote formation of iSNs from non-neuronal cells, as detailed below. Some other embodiments of the invention are directed to identifying compounds that can relieve pain and itch, or compounds that have unwanted off target effects causing pain and itch. In these embodiments, iSNs are first generated in accordance with the present invention. The cells are then contacted with candidate agents to identify compounds capable of modulating (e.g., inhibiting or enhancing) nociception/puritoception of the neurons. Still some other embodiments of the invention relate to identifying compounds that can relieve or cause degeneration of various sensory neurons types. Similarly, these methods entail first generating a specific sensory neuron type in accordance with methods of the invention. The induced neurons are then contacted with candidate agents to detect one or more compounds that are able to modulate (promote or suppress) the survival or function of the neurons.

Some other embodiments are directed to evaluating the phenotype of a genetic disease, e.g., to better understand the etiology of the disease, to identify target proteins for therapeutic treatment, to identify candidate agents with disease-modifying activity. These methods allow identification of compounds with desired therapeutic activities, e.g., an activity in modulating the survival or function of sensory neurons in a subject suffering from a neurological disease or disorder, e.g., to identify an agent that will be efficacious in treating the subject. For example, a candidate agent may be added to a cell culture comprising iSNs derived from the subject's somatic cells, and the effect of the candidate agent assessed by monitoring output parameters such as iSN survival, the ability of the iSNs to become depolarized, the extent to which the iSNs form synapses, and the like, by methods described herein and in the art. Detailed procedures for the various screening methods of the invention can be based on or modified from methods well known in the art, or the exemplified methods herein for identifying agents that promote iSN formation.

In the various applications of the iSNs of the invention, at least one parameter is monitored. The monitored parameter is a quantifiable component of cells, particularly a component that can be accurately measured, desirably in a high throughput system. The parameter can be any cell component or cell product including cell surface determinant, receptor, protein or conformational or posttranslational modification thereof, lipid, carbohydrate, organic or inorganic molecule, nucleic acid, e.g., mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, and etc. Characteristically a range of parameter readout values will be obtained for each parameter from a multiplicity of the same assays. Variability is expected and a range of values for each of the set of test parameters will be obtained using standard statistical methods with a common statistical method used to provide single values.

In some related embodiments, the invention provides kits or pharmaceutical combinations for generating iSNs and for using the iSNs in various applications described herein. Some of the kits will contain one or more components of the agents described herein for inducing formation of sensory neurons from non-neuronal cells. Any of the components described above may be provided in the kits, e.g., the specific BN1 or BN2 encoding polynucleotides or expressing vectors harboring them, packaging cell lines for producing recombinant viruses, as well as reagents for transducing recombinant viruses into a non-neuronal cell. The kits may further include non-neuronal cells for conversion into iSNs. The kits may also include tubes, buffers, etc., and instructions for use. The various components of the kits may be present in separate containers, or some or all of them may be pre-combined into a reagent mixture in a single container, as desired. In addition to the above components, the subject kits may further include instructions for practicing the methods of the invention. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), etc., on which the information has been recorded. Yet another form of these instructions that may be present is a website address which may be used via the internet to access the information.

VII. Screening for Factors that Stimulate Formation of iSNs From Non-Neuronal Cells Utilizing the system for generating iSNs described herein, the invention also provides methods to screen for compounds, cellular factors or modulations that can promote or stimulate conversion of a non-neuronal cell into iSN. The compounds or cellular factors or manipulations can be exogenous compounds and genetic or epigenetic modulations inside the non-neuronal cell. In these methods, co-expressing BN1 or BN2 in the non-neuronal cell is performed in the presence of the candidate compounds or cellular factors. This allows identification of specific candidate factor (e.g., a miRNA or an epigenetic modulation) which can enhance the efficiency of conversion of the non-neuronal cell into iSN. Various biochemical and molecular biology techniques or assays well known in the art can be employed to practice the screening methods of the present invention. Such techniques are described in, e.g., *Handbook of Drug Screening*, Seethala et al. (eds.), Marcel Dekker (1$P^{stP}$ ed., 2001); *High Throughput Screening: Methods and Protocols* (*Methods in Molecular Biology*, 190), Janzen (ed.), Humana Press (1$P^{stP}$ ed., 2002); *Current Protocols in Immunology*, Coligan et al. (Ed.), John Wiley & Sons Inc (2002); Sambrook et al., *Molecular Cloning: A Laboratory Manual*, Cold Spring Harbor Press (3$P^{rdP}$ ed., 2001); and Brent et al., *Current Protocols in Molecular Biology*, John Wiley & Sons, Inc. (ringbou ed., 2003).

The candidate compounds that can be screened for promoting iSN formation can be any polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, polynucleotides (e.g., miRNAs or siRNAs), polypeptides, saccharides, fatty acids, steroids, purines, pyrimidines, derivatives, structural analogs or combinations thereof. Some candidate compounds are synthetic molecules, and others natural molecules.

By way of example, the screening methods of the present invention typically involve inducing sensory neuron formation as described herein in the presence of candidate compounds or cellular manipulations (e.g., epigenetic modulations). Thus, co-expression of BN1 or BN2 genes in the non-neuronal cell (e.g., a fibroblast) is performed in the presence of the candidate compounds (e.g., miRNA) or performed in combination with other modulations (e.g., alternations in DNA methylation). If the presence of a candidate agent or modulation leads to an enhanced conversion efficiency of the non-neuronal cells into iSNs, the candidate compound (or the specific modulation) is then identified as an agent or factor that promotes formation of iSNs. An enhanced conversion efficiency refers to any substantial increase in the number of the initial non-neuronal cells being converted into iSNs. This can be an increase of at least 20%, at least 30%, at least 40%, at least 50%, at least 75%, or at least 90% or more, of the cells being converted into iSNs.

In some methods, various transcription factors or other polypeptides are screened for ability to promote iSN formation. Screen for iSN-promoting transcription factors or other DNA-binding proteins can be performed by using and/or modifying various assays that have been described in the art. See, e.g., Wiese et al., Front. Neurosci., 6:1-15, 2012; Alvarado et al., J. Neurosci., 31(12):4535-43, 2011; Ouwerkerk et al., Methods Mol. Biol., 678:211-27, 2011; Laurenti et al., Nat. Immunol. 14, 756-763, 2013; and Xu et al., Virol. 446:17-24, 2013. Some other methods of the invention are directed to identifying nucleic acid agents that are capable of stimulating formation of iSNs. For example, candidate miRNAs can be co-expressed inside the non-neuronal cell. Expressing miRNAs in a host cell and testing the miRNAs for ability to enhance iSN formation can be performed with techniques based on or derived from a number of miRNA screens that have been described in the literature. See, e.g., Voorhoeve et al., Cell, 124: 1169-1181, 2006; Becker et al., PLoS ONE 7(11): e48474, 2012; Lam et al., Mol. Cancer Ther. 9: 2943-2950, 2010; and Olarerin-George et al. BMC Biol., 11:19, 2013.

In still some methods, the candidate compounds are small organic molecules (e.g., molecules with a molecular weight of not more than about 500 or 1,000). Preferably, high throughput assays are adapted and used to screen for such small molecules. In some methods, combinatorial libraries of small molecule test agents can be readily employed to screen for small molecule modulators that enhance iSN formation. A number of assays known in the art can be readily modified or adapted in the practice of these screening methods of the present invention, e.g., as described in Schultz et al., Bioorg Med Chem Lett 8: 2409-2414, 1998; Weller et al., Mol Divers. 3: 61-70, 1997; Fernandes et al., Curr Opin Chem Biol 2: 597-603, 1998; and Sittampalam et al., Curr Opin Chem Biol 1: 384-91, 1997.

EXAMPLES

The following examples are offered to further illustrate, but not to limit the present invention.

Example 1. Some Experimental Techniques Used for Generating iSNs

Embryonic fibroblasts isolation and derivation: Wild-type CD1 mice were bred at the TSRI animal facility. MEFs were isolated from E14.5 embryos under a dissection microscope. The head, internal organs and spinal column containing the dorsal root ganglion was removed and discarded to eliminate cells with neurogenic potential. The remaining tissue was manually disassociated in 0.25% trypsin (Gibco) for 10 minutes at 37° C. subsequently the digestion solution was diluted and removed via centrifugation. The resulting cells were seeded at approximately $3 \times 10^6$ cells/cm$^2$. MEFs were grown to confluency and passaged at least twice prior to use. For HEF differentiation, human iPSCs colonies were harvested using 1 mg/ml collagenase type IV and differentiated by Embryoid Bodies formation. The EBs were cultured for 7 days in non-adherent suspension culture dishes (Corning), 2 days in 20% KSR medium and the following 5 days in 10% FBS DMEM. On day 8 the EBs were plated onto adherent tissue culture dishes and passaged according to primary fibroblast protocols using trypsin for three passages before the start of experiments.

Molecular cloning, cell culture and lentiviral infection: The cDNAs for human BRN3A (97% homologous to mouse Brn3a peptide), and mouse Ngn1, and Ngn2 were cloned into lentiviral constructs under the control of tetracycline operator (TetO) using the following primers: BRN3A forward and reverse respectively, 5'-ATGATGTCCAT-GAACAGCAAGCAG (SEQ ID NO:1) and 5'-TCAG-TAAGTGGCAGAGAATTTC (SEQ ID NO:2). Replication-incompetent VSVg-coated lentiviral particles were packaged in 293T cells as described in Boland et al. Nature 461, 91-94, 2009. Passage three CD1 MEFs were infected with lentivirus in MEF media (DMEM+10% fetal bovine serum and penicillin/streptomycin). After 12-16 hours of infection media-containing virus was replaced with fresh MEF media. Transcription factors were induced 48 hours post infection media by switching to MEF media supplemented with 5 µM doxycycline (Sigma). Four days after initiating induction with doxycycline media was replaced with N3 media (Vierbuchen et al., Nature 463, 1035-1041, 2010). Seven days post induction doxycycline was withdrawn unless otherwise stated. Ten days post-induction was switched to neural maintenance media, which consisted of a 1:1 mix of DMEM/F12 (Invitrogen) and Neurobasal supplemented with B27, and NGF, BDNF and GDNF, all at 10 ng/ml. Efficiency of conversion was measured by the number of Map2-positive cells divided by to the initial number of cells plated.

Immunohistochemistry, and RT-PCR: For immunofluorescence staining, cells were fixed 4% paraformaldehyde for 10 minutes at room temperature. Cells were then washed three times with PBS and subsequently permeabilized with 0.1% Triton X-100 (Sigma) in PBS. After washing and permeabilization cells were blocked in 5% horse serum for thirty minutes at room temperature. Primary staining was performed overnight at 4° C. in block. Secondary antibodies were diluted in blocking solution and stained room temperature for one hour. EdU staining was performed using Click-it EdU kit (C10337;Invitrogen) following manufacturer's instructions. The following antibodies and dilutions were used: Ms-βIII-Tubulin (Tuj1) (1:1000, Covance MMS-435P); (Tuj1) (1:1000, Covance MRB-435P); Ms-Map2 (1:500, BD 556320); Ms-VGlut1 (1:100, Millipore MAB5502); Rb-Vglut2 (1:50, abeam ab72310); Gp-VGlut3 (1:1000, Millipore AB5421); Ms-Brn3a (1:200, Millipore MAB1585); Gt-human Ret (1:100, R&D AF1485); Gt-mouse Ret (1:100, R&D AF482); Ms-Islet1 (1:200, DSHB 40.2D6); Gt-mouse TrkB (1:200, R&D BAF1494); Gt-TrkA (1:200, R&D AF175); Sh-TrkC (1:200, Abeam ab72120); Ms-NF200 (1:200, Millipore MAB5266); Rb-Runx1 (1:100, Novus Bio NBP1-61277); Rb-Peripherin (1:200, Millipore AB1530); Gaba (Sigma), Nng1 (1:500 Abeam), Ngn 2 (1:500 Millipore), P75 (Abeam), CGRP (1:500 Neuromics), Substance P (1:500 Neuromics), VAMP (Synaptic systems), Synapsin (Synaptic systems). Secondaries: A21447D-G647 A10036-DM546 A21202-DM488 A10040-DR546 A11015-DSh488 A11056-DGt546 A21206-DRb488 A21208-DRt488 A21098-DSh546.

For RT-PCR analysis total RNA was isolated at the time-points indicated using Trizol (Invitrogen) following manufacturer's instructions, treated with DNaseI (Ambion) and 1.0 µg was reverse transcribed with iScript (BioRad). PCRs were performed using TaqMan Gene Expression Assays (Applied Biosystems) or SYBR green. For quantitative RT-PCR from single cells, single cells were grown on glass coverslips from which they were isolated three weeks after induction using a using a patch pipet and micromanipulator. Cells were placed in 4 µl of lysis/RT buffer consisting of Superscript III RT buffer (Invitrogen) supplemented with 0.5% NP-40, 1 mM DTT, and SuperRnase inhibitor (Ambion), and Prime RNase inhibitor (5 Prime). Cells were spun down in a microcentrifuge and flash frozen at −80° C. until further processing. Reverse transcription was performed using SuperScript III (Invitrogen) with 130 nM of each gene-specific 3'-primers. Reverse transcription products were than subjected to 15-cycles of target specific pre-amplification using 15 nM of outside nested primers designed to produce amplicons of 300-400 bp. A quantitative real-time PCR with was subsequently performed using SYBR select (Applied Biosystems, 4472918) with internal primers designed to generate amplicons approximately 100 base pairs. To ensure specificity template titrations were performed and only primers that demonstrated linear amplifications were used melt-curves were also obtained for single cells and controls to ensure specificity of products.

Calcium imaging and electrophysiology: Calcium imaging was performed on mouse and human iSNs 2 to 3 weeks post-induction using Map2::GCAMP5.G lentiviral reporter (Addis et al., PLoS ONE 6, e28719, 2011). Imaging was performed in Tyrode's solution (145 mM NaCl, 2.5 mM KCl, 10 mM Hepes, NaH$_2$PO$_4$, 2 mM CaCl$_2$, 1 mM MgCl$_2$, 10 mM Glucose, and 0.4 mM ascorbic acid) at a constant flow rate of 250 ml/hour. To monitor calcium response, capsaicin, menthol, and mustard oil were added sequentially in randomized orders to the flow chamber at a 10× concentration to deliver a final concentration of 10 µM capsaicin, 100 µmM menthol, and 100 µM mustard oil. Each tracing experiment was bracketed by an initial and final pulse of 5 mM KCl to confirm neural identity and sustained functional ability. Only cells with neural identity and sustained functional ability were analyzed. Calcium responses were determined by calculating the change in fluorescence over the initial fluorescence $(F-F_0)/F_0$, where F=the fluorescence at a given time point and $F_0$=the mean basal, unstimulated fluorescence of each cell. A typical non-response area was selected for fluorescence bleed normalization and background subtraction.

Electrophysiology: Fibroblasts were plated, transduced and cultured on laminin coated thermanox plastic coverslips (13 mm) as described in cell culture methods. Coverslips were placed in the recording chamber mounted on an Olympus IX 71 microscope. Spontaneous or evoked responses were recorded at room temperature via whole-cell recording with a patch electrode. Signals were amplified using an Axopatch200B and MultiClamp700B (Axon Instruments) and filtered at 2 KHz via a Bessel low-pass filter. Data were sampled and analyzed using pClamp10.1 software in conjunction with a DigiData interface (Model 1322A, 1440A Axon Instruments). Patch pipettes were pulled from standard wall glass of 1.5 mm OD (Warner Instruments) and had input resistances of 5-11 M. In general, for recording voltage-gated currents and action potentials, patch electrodes were filled with the following solution (in mM): 140 K-gluconate, 5 NaCl, 1 MgCl2, 10 EGTA, 10 HEPES, 10 EGTA; pH adjusted by KOH to 7.25, osmolarity measured at 290 mOsm. For isolation of $Na^+$ current from $K^+$ current, cesium was substituted for potassium as the major cation in the patch pipette-filling solution in order to suppress $K^+$ currents. The composition of the intracellular solution used for recording ligand-gated currents was as follows (in mM): 130 Cs-gluconate 2 MgATP, 1 MgCl2; 10 EGTA; 10 HEPES; pH 7.25, osmolarity 300 mOsm. Foe evoked action potentials we started recordings in the current clamp mode at the resting membrane potential values and use artificial hyperpolarization by negative current injection with Δ level of 25 pA. The bath solution generally contained a Na+ saline based Hank's balanced salt solution (pH=7.3). To monitor voltage-gated currents, after initial pre-hyperpolarization to -90 mV for 300 ms to relieve Na inactivation, we applied step potentials ranging from -60 to +30 mV for 100 ms.

Example 2. Generation of Sensory Neurons from Mouse Embryonic Fibroblast

Figure 1:
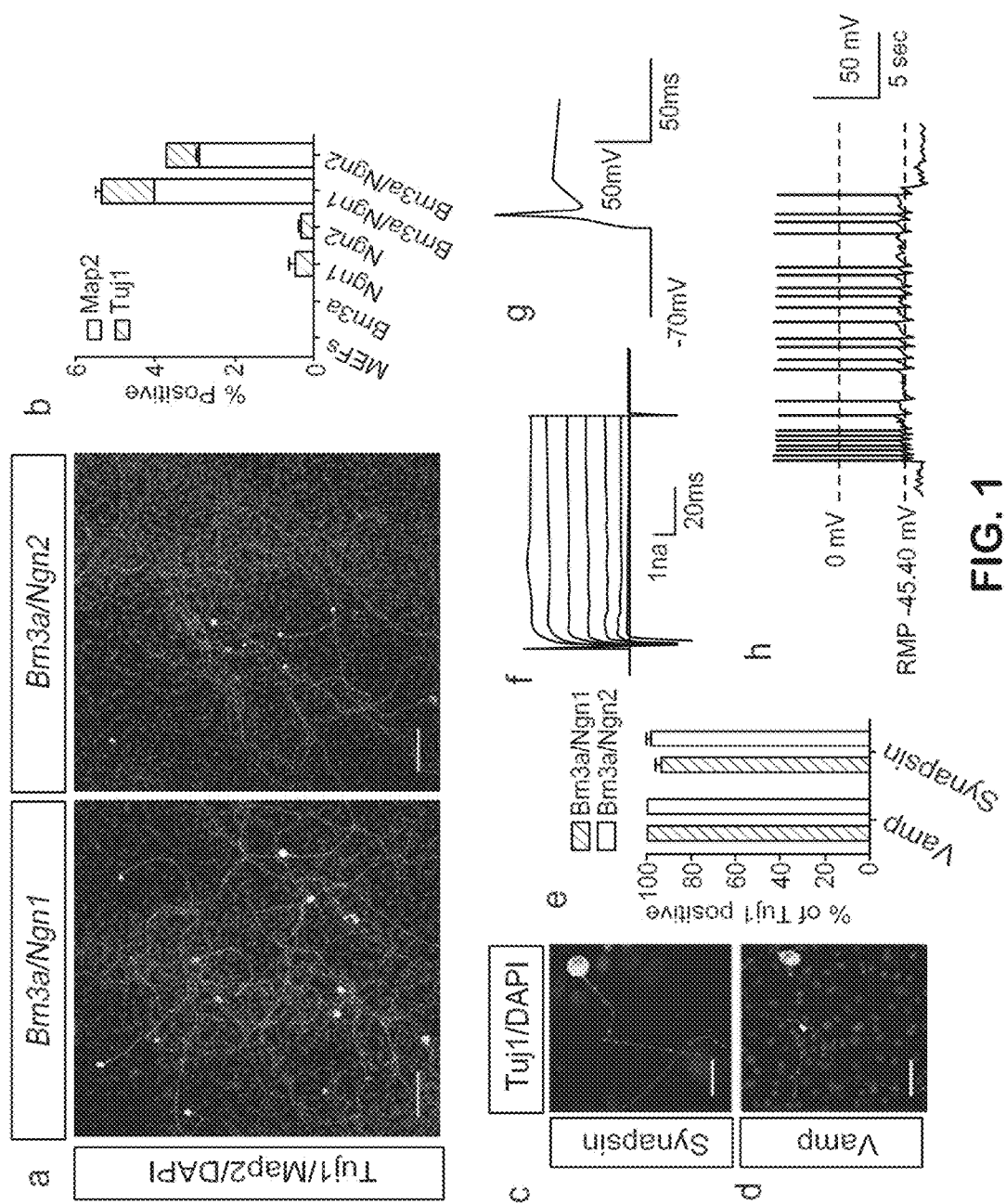
FIGS. 1A-1H show that transient co-expression of two developmentally relevant transcription factors stably reprograms fibroblasts to attain properties of functionally mature neurons. (a) Transient co-expression of Brn3a with either Nng1 or Ngn2 for 8 days in fibroblasts induces cells with neural morphology that stain for pan-neural markers Map2 and Tuj1 Cells were immunostained 14 days post-induction. Scale bar: 100 μm. (b) Cooperative expression of Brn3a with Nng1 or 2 is required for induction of Map2/Tuj1 double positive cells. TFs were induced for 8 days and immunostained 14 days post-induction. Bars and error represent means and SEMs from three replicates. (c) Synapsin expression in BN2 neural cells, cells were counterstained for pan-neural marker Tuj1. (d) Vamp expression in BN1 neural cells. Scale bars: 25 μm (e) The majority of neurons induced with BN1 and BN2 express synaptic marker indicative of mature neurons. Bars in graphs represent means and error bars represent±SEM. (f) Whole-cell currents recorded in voltage-clamp mode. Inward fast inactivating Na$^+$ and outward currents are observed. (g) Representative action potential evoked from MEFs after 14 days in culture. (h) A train of spontaneous action potentials observed in 14-day culture.

To determine whether we could produce induced neurons using factors involved in the development of the somatic sensory neural lineage, we used lentiviral vectors to express either Brn3a and Nng1 (BN1) or Brn3a and Ngn2 (BN2) in mouse embryonic fibroblasts (MEFs). Reprogramming factor expression was controlled temporally by coinfecting with a lentivirus encoding the doxycycline inducible factor rtTA and placing the BN1/BN2 factors under control of the doxycycline inducible promoter TetO (FIGS. 8a and b). After eight days of induction we removed doxycycline and allowed cells to mature without further expression of the exogenous reprogramming factors. Both the BN1 and BN2 conditions produced numerous Tuj1 positive cells exhibiting neuronal morphology and the majority of these cells also expressed Map2 (FIG. 1a-b and FIG. 8b). This conversion requires both factors. Expression of either Nng1 or Ngn2 alone induced Tuj1-positive cells, however, these cells did not express Map2 and did not exhibit neuronal morphologies. No TuJ1 or Map2 positive cells were found in untreated MEFs or those exposed only to Brn3a (FIG. 8b). Immunostaining further confirmed that >98% of Map2/Tuj1 double positive cells induced by Brn3a/Ngn1 or Brn3a/Ngn2 expressed synapsin and synaptobrevin (also called VAMP) consistent with a relatively mature neural state capable of forming functional synapses (FIG. 1c-e).

To determine whether BN1 and BN2 neural cells exhibit membrane and electrophysiological properties of neurons, we performed whole-cell patch-clamp recordings. The average resting membrane potential of neural cells induced by BN1 or BN2 was -42.01 mV (SEM=1.74, n=4) which is similar to resting potentials reported for other induced neurons (Vierbuchen et al., Nature 463, 1035-1041, 2010). Depolarizing in voltage clamp mode elicited fast inward currents followed by slow outward currents consistent with opening of voltage-activated sodium and potassium channels, respectively (n=5; FIG. 1f). Of the five cells that exhibited Na+/K+ currents, four were able to fire evoked action potentials and one of these cells also exhibited spontaneous firing. (FIGS. 1g and h). Taken together, these data show that BN1 and BN2 are sufficient to reprogram fibroblasts to neuronal cells with synaptic and electrophysiological properties consistent with a neuronal identity.

Figure 2:
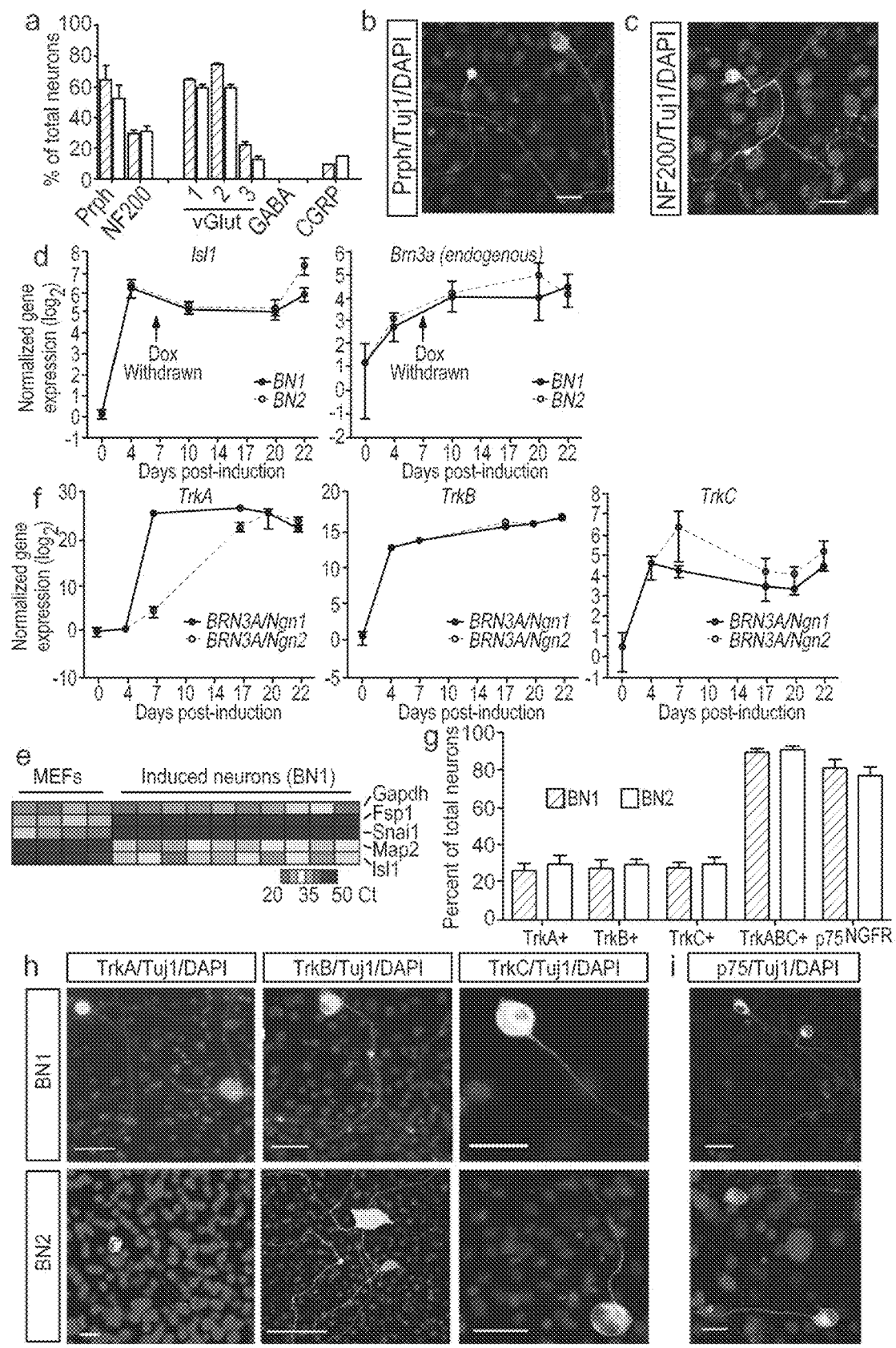
FIGS. 2A-2I show that neurons induced with BN1 or BN2 exhibit molecular hallmarks of the somatic sensory neural lineage. (a) Quantification of neurofilaments, neurotransmitters, and neuropeptide expression in BN1 and BN2 neurons. Expression was assessed 20 days post induction via immunostaining. Bars represent mean, error bars represent SEM from at least 100 cells. (b) A subset of neurons induced via BN1 or 2 express the peripheral neurofilament peripherin. Scale bar: 25 μm. (c) A subset of neurons induced via BN1 or 2 express the peripheral neurofilament NF200. Scale bar: 25 μm. (d) Time course of quantitative RT-PCR analyses of Isl1 and endogenous Brn3a expression following induction of Brn3a/Ngn1 or Brn3a/Ngn2. Fold-induction calculated as the increase in expression from un-induced fibroblasts cultured for the same duration in the same conditions for each time-point. Doxycycline was withdrawn permanently eight days post-induction as indicated with the arrow. (e) Single cell quantitative RT-PCR for of induced neurons 20 days post-induction. (f) Fold-induction of TrkA, B, and C following induction of Brn3a/Ngn1 or Brn3a/Ngn3. Fold-induction is calculated as the increase in expression from un-induced fibroblasts cultured for the same duration in the same conditions for each time-point. (g) Quantification of neurons positive for p75 and each of the three Trk receptors individually and combined. Bars represent means and error bars represent SEM from two independent experiments in which a minimum of 150 cells were counted. (h) Representative immunostaining for Trk A, B, and C 20 days post-induction. (i) p75 immunostaining 20 days post induction. Scale bar: 25 μm.

The neurons induced with BN1 or BN2 exhibit molecular hallmarks of the somatic sensory neural lineage. To determine the extent to which neurons induced by BN1 or BN2 resemble endogenous somatic sensory neurons, we examined expression profiles of neurofilaments neurotransmitters, and neuropeptides commonly used to characterize populations of these neurons. Within the DRG, distinct populations of sensory neurons, thin (C-fiber) and thick (A-fiber), can be identified by their expression of either peripherin or NF200, respectively. Peripherin is a type-III neuron specific intermediate filament found primarily in the peripheral nervous system. Approximately 60% of DRG neurons express peripherin, which corresponds to small diameter unmyelinated neural populations. Similar to DRG neurons, 50-60% of induced neurons (BN1=64.17%±9.67; BN2=51.93%±9.12) expressed peripherin (FIGS. 2a and b). The majority of remaining non-peripherin positive neurons express the heavy neurofilament NF-200 (also called NF-H), corresponding to thick myelinated fibers. Similar to endogenous DRGs, approximately 30% of iSNs (BN1=29.38±1.46; BN2=30.60±3.11) expressed NF200 (FIGS. 2a and c). These data demonstrate that the BN1 and BN2 transcription factor combinations both induce neurons to express neurofilaments typically found in peripheral sensory neurons in similar proportions to those observed in the DRG. Somatic sensory neurons are excitatory glutamatergic neurons that express three vesicular glutamate transporters 1, 2 and 3 (also known as vGlut1(Slc17a7), vGlut2(slc17a6), and vGlut3(slc17a8), respectively). Consistent with a somatic sensory neural identity, the induced neurons expressed all three vesicular glutamate transporters but did not express GABA, demonstrating that this conversion produces excitatory but not inhibitory neuronal subtypes (FIG. 2a; and FIG. 9a). In the DRG a subset of nociceptive neurons also express the neuropeptide CGRP. We observed CGRP expression in approximately 10% of induced neural cells (FIG. 2a; and FIG. 9a). These data demonstrate that neurons induced with BN1 and BN2 express characteristic neurofilaments, neurotransmitters and peptides found in peripheral sensory neurons.

Mature peripheral sensory neurons express the transcription factors Isl1 and Brn3a but no longer express Nng1 or Ngn2. During reprogramming with either BN1 or BN2 both Isl1 and endogenous Brn3a expression are strongly up regulated and this expression is maintained for at least 14 days after doxycycline withdrawal (FIG. 2d). In contrast, Nng1 and Ngn2 were no longer detectable after exogenous induction was extinguished (FIG. 9b). Treatment with BN1 or BN2 did not induce the expression of various markers of other neuronal subtypes such as Satb2, Ctip2, Brn2, Tbr2, and Tbx21 (data not shown). Finally, single cell RT-PCR confirmed that induced neurons that have up regulated Map2 and Isl1 have also down-regulated the fibroblast specific genes Snai1 and Fsp1 (FIG. 2e). These data further support the conclusion that BN1 and BN2 reprogram fibroblasts to assume and maintain a neural identity consistent with that of endogenous somatic sensory neurons.

In vivo, selective expression of one of the three Trk receptors, TrkA, TrkB, and TrkC is critical for proper target innervation, survival, and expression of downstream molecular programs that distinguish the three lineages of sensory neurons. Quantitative RT-PCR showed that mRNA for TrkA, TrkB and TrkC was present as early as 4 days post induction in both the BN1 and BN2 conditions. Trk receptor mRNA levels reach a plateau after 7 days, which is maintained for at least 22 days, showing that conversion has become independent of the inducing factors. (FIG. 2f). Immunostaining confirmed that TrkA, TrkB, and TrkC proteins are present in the soma and along the axons of neurons induced with either BN1 or BN2 at 16 days post induction (FIG. 2h). Immunostaining for each of the Trk receptors labels approximately 25-30% of the induced neurons (FIG. 2g), suggesting that they may each comprise a distinct non-overlapping subpopulation as is seen in vivo.

To establish whether the Trk-staining corresponded to one homogenous population expressing all three receptors, or three unique populations each expressing one of the three Trk-receptors; we simultaneously co-stained for TrkA, B and C and each pair-wise combination of the three receptors. Each pair-wise combination of TrkA, B, and C stained approximately 60% of neurons induced by BN1 and BN2 (FIG. 9c). In contrast, simultaneous co-staining for all three Trk receptors labeled approximately 90% of induced neurons (BN1=88.95%±2.17; BN2=91.09%±1.80) (FIG. 2g). In the DRG most of the sensory neurons also express the $p75^{Ngfr}$ the low-affinity NGF receptor. In our experiments the majority (>80%) of total neurons induced by BN1 and BN2 express $p75^{Ngfr}$ (FIGS. $2_g$ and i). Together, these results suggest that TrkA, TrkB, and TrkC-positive cells represent three distinct populations that constitute the majority of neurons induced by BN1 and BN2. Because neurons induced by BN1 or BN2 express transcription factors, neurofilaments, neurotransmitters and neuropepetides, characteristic of somatic sensory neurons and selectively express one of the three major Trk receptor lineage markers, we chose to designate this neural population as induced sensory neurons (iSNs) or induced somatic sensory lineage neurons (iSLNs). Intriguingly, although in vivo studies suggest that Ngn1 and Ngn2 expression might bias differentiation to different Trk receptor sublineages, treatment with BN1 and BN2 produced equal proportions of cells expressing each lineage marker across multiple experiments (Ma et al., Genes Dev. 13:1717-28, 1999).

Example 3. Characterization of iSNs Generated from MEFs

Figure 3:
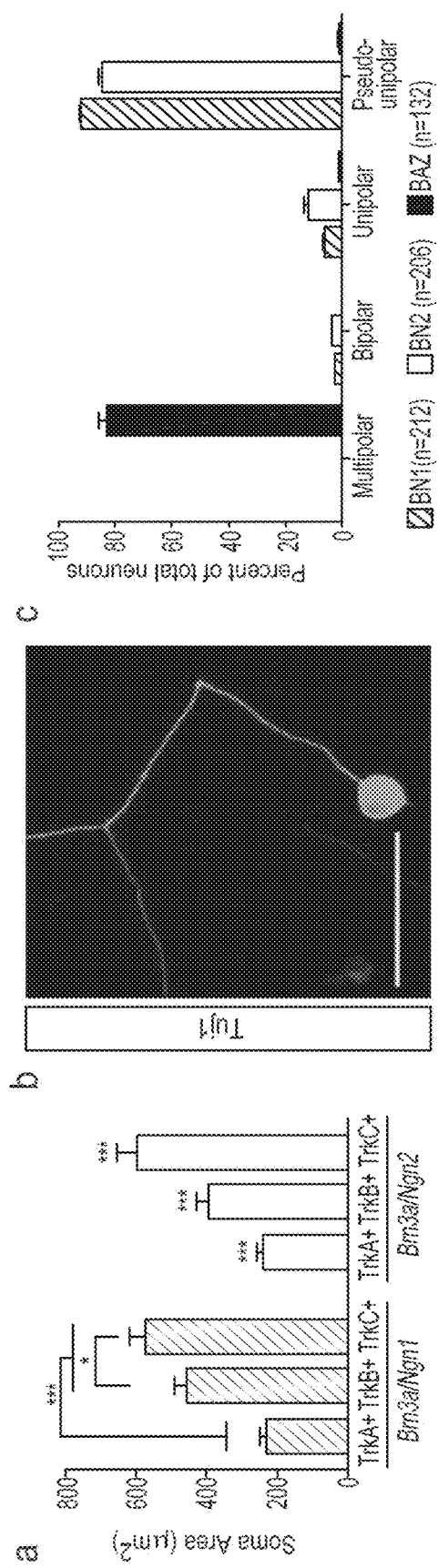
FIGS. 3A-3C show that reprogramming induces somatic sensory neural morphology. (a) TrkA, TrkB, and TrkC immunoreactive neurons have distinct distribution of soma size. Graph depicts mean soma areas by Trk immune-reactivity. Error bars represent ±SEM. *$p<0.001$; $p<0.01$(one-way ANOVA with Newman-Keuls post-hoc comparison) (b) Typical morphology of pseudounipolar cells induced by BN1 and BN2. Scale bar: 100 μm (c) The majority of Map2/Tuj1-positive cells induced via Brn3a/Ngn1 or Brn3a/Ngn2 are pseudo-unipolar. The figure shows quantification of the neural morphologies observed in representative experiments fourteen days post-induction. Bars represent means from two independent experiments.

We observed that the reprogramming described herein induces somatic sensory neural morphology. In vivo, sensory neurons also vary with respect to the size of their cell body. TrkA-positive neurons are the smallest, TrkB-positive neurons are intermediate, and TrkC-positive neurons comprise a population with the largest cell bodies. To determine whether iSNs generated with either BN1 or BN2 also adopt this morphological signature we measured the area of TrkA, B, and C-positive neurons. The induced neurons generated by both BN1 and BN2 exhibited distinct distributions of soma size that correlated with expression of TrkA, TrkB, and TrkC (FIG. 3a, and FIG. 10a-b). The mean soma area of TrkA-positive cells (BN1=231.3 μm±14.02; BN2=237.8 μm±21.87) was significantly smaller than TrkB-positive cells (BN1=456.2 μm±34.38; BN2=397.5 μm±30.69). Likewise, the mean soma area of TrkB-positive cells was significantly smaller than TrkC-positive neurons (BN1=569.9 μm±47.01; BN2=598.5 μm±53.29) (FIG. 3a, and FIG. 10a-b). These results further suggest that the TrkA, B and C positive cells we observed represent three distinct populations.

Sensory neurons of the DRG also exhibit a unique pseudounipolar morphology characterized by the absence of dendrites and presence of a single bifurcating axon. Visual inspection of the neurons induced by BN1 and BN2 suggested that they had adopted this morphology (FIG. 3b). Therefore we quantified the number of multipolar, bipolar, unipolar, and pseudounipolar neurons generated from two independent experiments using BN1 and BN2. Remarkably, the majority of induced neurons (BN1=91.99%±0.40; BN2=84.69%±1.357) exhibited a pseudounipolar morphology (FIG. 3c and FIG. 10c). The remaining neural cells were either unipolar without observable bifurcation (BN1=6.13%±0.414; BN2=11.89%±1.43), or bipolar (BN1=1.89%±0.02, BN2=3.4%±0.08) (FIG. 3c). In contrast, as reported previously, neurons generated using Brn2, Ascl1, and Zic1 (BAZ) were primarily multipolar (Vierbuchen et al., Nature 463, 1035-1041, 2010); no pseudounipolar neurons were observed using these factors (FIG. 3c). This finding demonstrates that direct reprogramming with only two transcription factors can induce a highly specific neurite morphology distinct from that produced by previous methods, predicting that exogenous cues such as appropriate targets or glial derived factors are not required for this aspect of neuronal specification.

Figure 4:
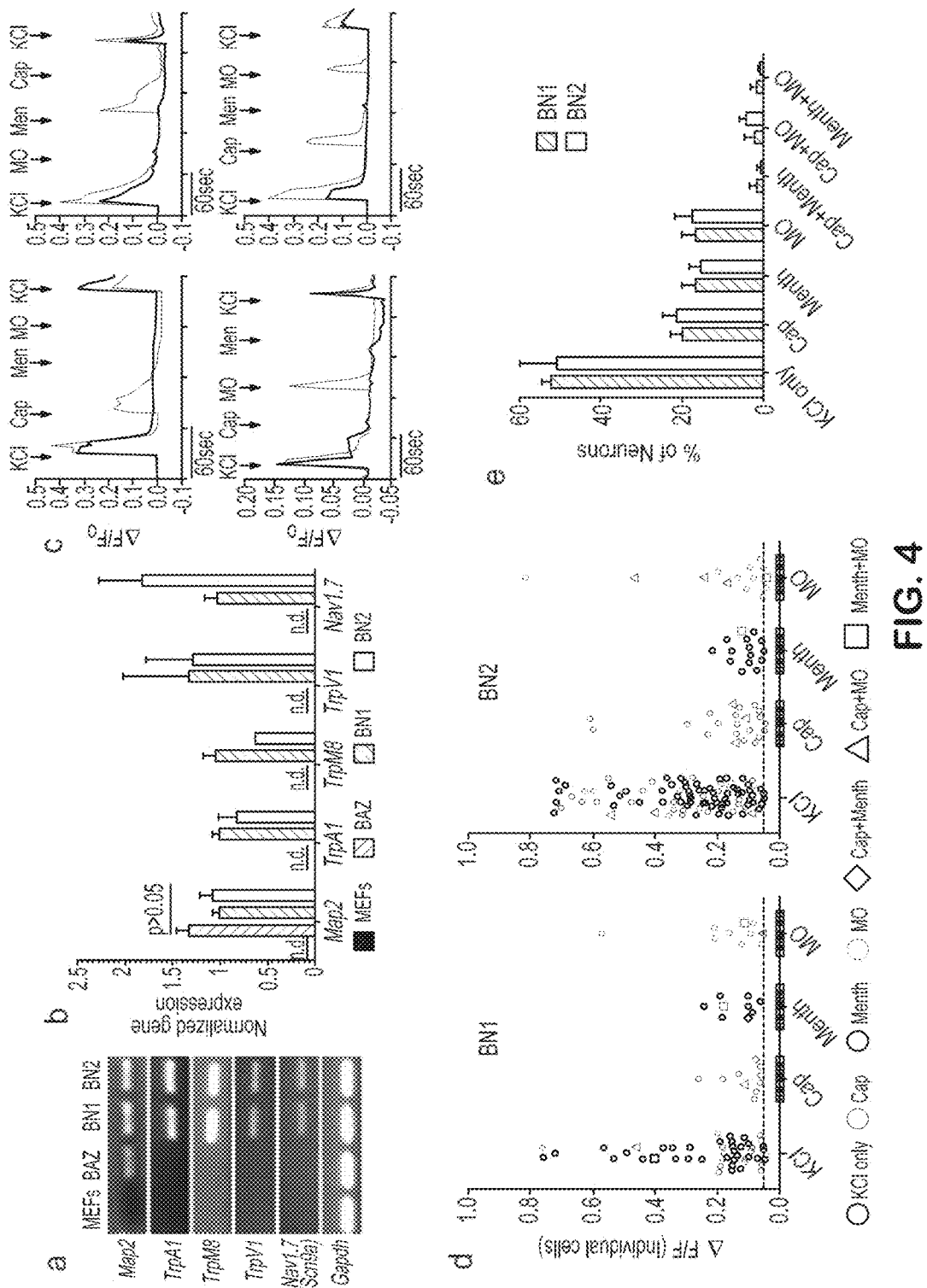
FIGS. 4A-4E show that iSNs posses functional properties of sensory neurons. (a) RT-PCR analysis of MEFs, neurons induced with BAZ and iSNs generated with BN1 or BN2. TrpA1, TrpM8, TrpV1 and Na$_v$1.7 are detected in BN1 and BN2 but not in MEFs or BAZ. (b) Quantitative RT-PCR of MEFs, neurons induced with BAZ and iSNs generated with BN1 or BN2. BAZ, BN1 and BN2 samples expressed similar levels of Map2. TrpA1, TrpM8, TrpV1 and Na$_v$1.7 are present in BN1 and BN2 however not detected in MEFs or BAZ samples indicated by n.d. Expression is normalized to Gapdh. Expression levels are relative to BN1 such that expression of BN1=1.0. Bars and error bars represent means and SEMs from two independent biological replicates. (c) Representative calcium responses for 10 μM capsaicin (Cap), 100 μM Menthol (Menth), and 100 μM mustard oil (MO). Calcium transients were measured using Map2::GCAMP5.G. Calcium responses were calculated as the change in fluorescence (ΔF) over the initial fluorescence (F$_o$). Depolarization with 2.5 mM KCl was used at the beginning and end of each experiment to confirm neural identity and sustained functional capacity. (d) ΔF/F$_o$ intensity plot showing the response of individual cells to each ligand. Each cell is represented in each column. Cells respond to either KCl only (black circle), KCl plus one other ligand (other circles), or KCl plus two other ligands (diamond, triangle or square). (e) Distribution of KCl responders that responded to either KCl only, KCl plus one other ligand, or KCl with two other ligands. Bars represent means from at least four experiments. Error bars represent SEM.

We also found that the induced iSNs include cells that resemble different populations of nociceptors. The utility of iSNs for mechanistic and screening studies depends on the ability of these neurons to recapitulate functional properties of biomedically relevant neural subtypes. Assays for distinguishing functional properties of sensory neurons are predominately limited to the TrkA nociceptive sub-lineage because TrkC lineage proprioceptive function requires muscle innervation and the mechanical responses of the TrkB lineage are similar to the inherent mechanical responses of fibroblasts. Therefore we focused on establishing the functional responses of the TrkA lineage of nociceptive neurons. TrkA positive neurons in the DRG and trigeminal nerve detect sensations such as pain and temperature in part by expressing various combinations of members of the Transient receptor potential (Trp) family of ion channel receptors. To determine whether iSNs exhibit key functional properties of sensory neurons, we first assessed expression of receptor ion channels TrpV1, TrpM8, and TrpA1, which mediate a broad spectrum of sensations such as heat, cold, and noxious chemicals, respectively. Uninfected MEFs, and neurons induced with the proneural cocktail Brn2, Mash1, Zic1 (BAZ) failed to express any of the Trp channels (FIGS. 4a and b). However, iSNs induced with either BN1 or BN2 robustly expressed TrpA1, TrpM8, and TrpV1 (FIGS. 4a and b). In addition, BN1 or BN2 iSNs selectively expressed the voltage-gated sodium channel Nav1.7 (also called Scn9a) known to play a critical role in the generation and conductance of action potentials in nociceptive neurons (FIGS. 4a and b). Collectively, these data predict that some iSNs should be able to sense and respond to stimuli such as heat, cold and pungent natural compounds.

To determine whether iSNs can respond functionally to Trp channel ligands, we evaluated calcium transients following exposure to allyl isothiocyanate (mustard oil), menthol, and capsaicin at concentrations known to selectively activate TrpA1, TrpM8 and TrpV1, respectively. Following an initial depolarization using 2.5 mM KCl to identify responsive iSNs, cells were serially washed with menthol, mustard oil, and capsaicin in a randomized order. Both BN1 and BN2 iSNs exhibited rapid transient calcium fluctuations in response to capsaicin (BN1 19.7%±3.0 and BN2 21.2%±3.5); menthol (BN1 15.4%±2.6 and BN2 17.4%±4.3); mustard oil (BN1 12.9%±3.8 and BN2 12.5%±3.4) (FIG. 4c-e). Although the majority of ligand responsive iSNs were responsive to only one ligand, a few iSNs responded to two ligands sequentially: capsaicin and menthol (BN1 1.7%±1.7% and BN2 0.7%±0.7); capsaicin and mustard oil (BN1 2.3%±2.3 and BN2 4.1%±1.7); menthol and mustard oil (BN1 1.7%±1.7 and BN2 0.7%±0.7). No iSNs responded to all three sensory ligands. While the relative proportions of cell responsive to various combinations of stimuli differs from those seen in vivo, these results demonstrate that iSNs can diversify and express the primary receptors and signaling pathways required to selectively respond to biomedically-relevant sensory stimuli.

Example 4. Reprogramming Does Not Require Cell Division or Embryonic Precursors

Figure 5:
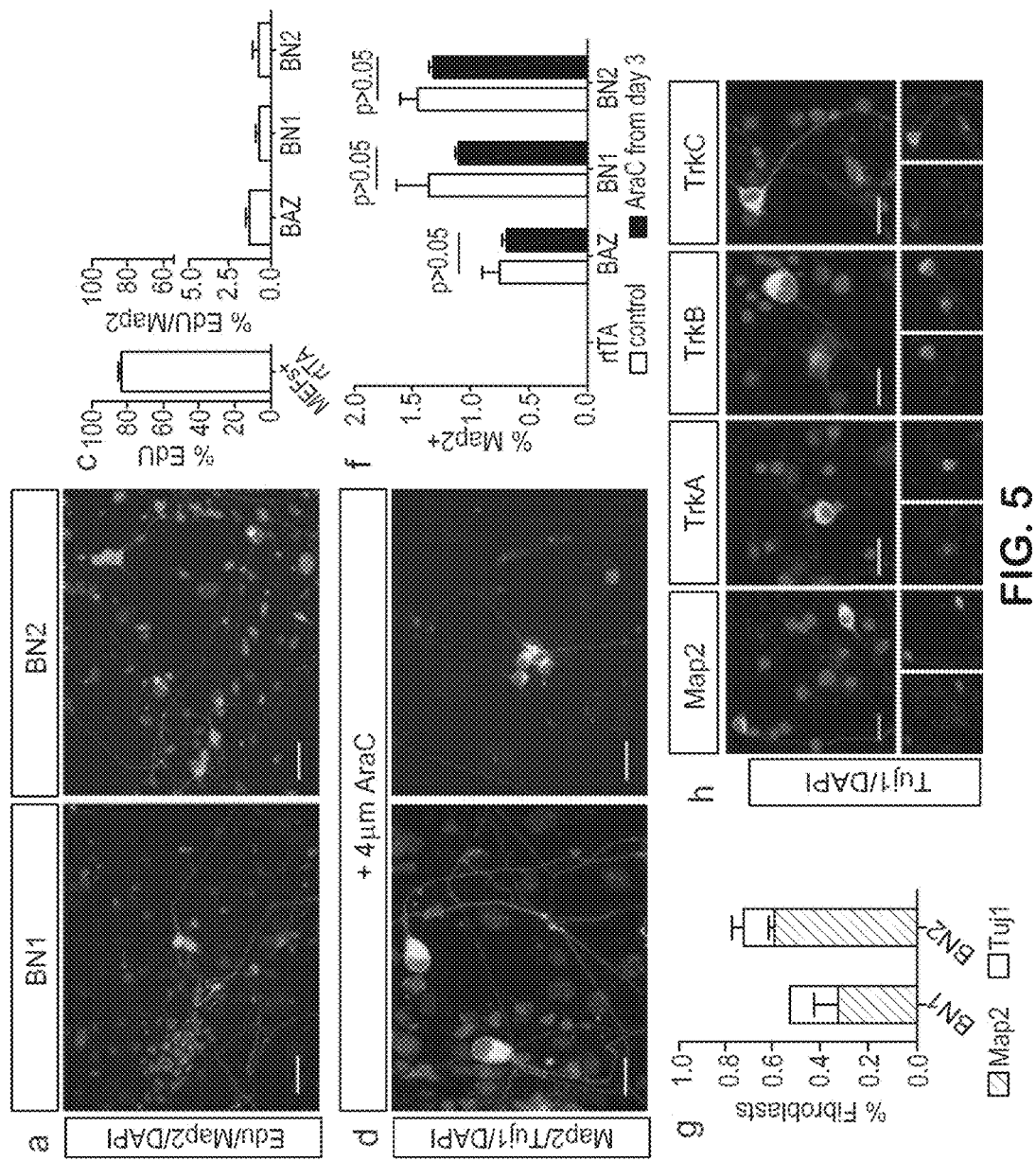
FIGS. 5A-5H show that induction of the somatic sensory lineage does not require cell division or specialized embryonic cells. (a and b) EdU and Map2 staining fourteen days post induction. (c) Quantification of the number of Map2-positive cells that co-stained for the mitotic indicator EdU. rtTA are MEFs infected with reverse tetracycline transactivator. BAZ is MEFs infected with Brn2, Mash1 (also known as Ascl1) and Zic1 a previously reported transcriptional cocktail for the direct conversion of MEFs to neurons[10]. Bar are means from two separate experiments. Error Bars are SEM. Scale bar: 25 μm (d and e) BN1 and BN2 generate neurons in the presence of the mitotic inhibitor AraC. AraC was applied from three days post induction until the end of the experiment at 4 μM, a concentration empirically determined to inhibit >90% proliferative cells. (e)

We examined whether the observed reprogramming of fibroblasts to the somatic sensory lineage requires cell division or specialized embryonic precursors. The induction of BN1 or BN2 in fibroblasts results in the production of multiple related subtypes of neurons (either TrkA, TrkB or TrkC positive), which seem to arise in roughly equivalent numbers. One possible explanation for this would involve a multipotent proliferating precursor cell that differentiates into these three subtypes. To address this possibility we performed two experiments. First, MEFs were reprogrammed in the presence of the proliferation marker EdU (5-ethynyl-2'-deoxyuridine, a click-chemistry BrdU analog). Addition of EdU to the culture media three days post induction labeled fewer than 0.5% of the total Map2-positive iSNs after 14 days of reprogramming, suggesting that BN1 and BN2 neural conversion does not involve proliferation (FIG. 5a-c). Second, to further block proliferation we applied the mitotic inhibitor arabinofuranosyl cytidine (AraC) to cultures continuously from three days post induction and quantified the number of Map2-positive cells on day 14. Consistent with the absence of a proliferative intermediate, mitotic inhibition from day 3 did not significantly alter the number of neurons that were produced during reprogramming (FIG. 5d-f). These data indicate that cell division is not required for induction of iSNs and predict that the diversification of neurons may involve a stochastic cell fate choice that operates in a non-dividing cell.

While the frequency of iSNs that arise using this protocol is relatively high (~1-10%) and varies depending on viral titer, it remains possible that this conversion requires a particular embryonic cell type that could be "pre-committed" to this lineage. To test this we derived tail-tip fibroblasts (TTFs) from 5-day old pups. Staining for markers of neural precursors showed that these cultures did not contain neural progenitor (data not shown). When TTFs were exposed to BN1 or BN2 for eight days, and cultured without doxycycline induction for an additional 7 days, Map2/Tuj1-positive cells were observed. As previously observed, these cells exhibited pseudounipolar morphologies consistent with sensory neural identity (FIGS. 5g, h). Furthermore, neural cells induced with both BN1 and BN2 expressed all three of the TrkA, B, and C receptors (FIG. 5h). These results demonstrate that the ability of BN1 and BN2 to generate neurons is not restricted to embryonic tissues and that iSNs can indeed be generated from adult fibroblasts.

Example 5. Generation of iSNs from Human Fibroblasts

We further sought to determine whether this method could be applied to human cells. Human embryonic fibroblasts (HEFs) were derived from iPSCs using established methods (Son et al., Cell Stem Cell 9, 205-218, 2011). HEFs were transduced with inducible lentiviral vectors encoding either BN1 or BN2 and the doxycycline dependent activator rtTA as described in the mouse reprogramming experiments. Transcription factor expression was induced for eight days, followed by at least seven days removal from doxycycline induction. Fifteen days after induction, we observed MAP2/TUJ1-postive cells with neuronal morphologies in the BN1 and BN2 conditions, but not in control uninfected HEFs or in HEFs treated with single transcription factors (FIG. 6a-b). Similar to mouse iSNs, human BN1 and BN2 induced neurons exhibit mRNA and protein expression of somatic sensory lineage markers TrkA, B, and C (FIGS. 6c-e, m). Immunostaining of iSNs shows that TRKA (BN1 33.6%±6.2, BN2 35.8%±7.6), TRKB (BN1 28.6%±5.6, BN2 29.0%±0.5), and TRKC (BN1 30.0%±7.6, BN2 32.3%±1.7) are each expressed in approximately one third of the population (FIGS. 6c-e, n). Additionally they showed nearly ubiquitous expression of the transcription factor ISL1 (BN1=93.15%±4.14; BN2=90.5±5.14) (FIGS. 6f, n). These markers were absent in neurons derived using the pan-neural cocktail Brn2, Ascl1, and Zic1 (BAZ) (FIG. 6n). However, both BN1/2 and BAZ neurons were shown to be mostly glutamatergic through immunostaining of vGLUT2 (FIGS. 6g, n). This suggests that a sensory neural phenotype is selectively imparted to human fibroblasts by transient ectopic expression of Brn3a with either Nng1 or Ngn2.

We further characterized the BN1 and BN2 iSNs and observed strong expression of low-binding NGF receptor p75 in nearly all iSNs (FIGS. 6k and 6o), and expression of the GDNF receptor c-RET in a subset of iSNs (FIGS. 6j and 6o), which was absent from the mouse iSNs for unknown reasons. Furthermore, neural populations of iSNs expressed the characteristic neurofilaments, peripherin and NF200 that are associated with thin and thick fiber neurons, respectively (FIGS. 6h, 6i, and 6o). Additionally BN1 and 2 showed expression of vGLUT1 (FIGS. 6l and 6o) and a complete absence of GABA (data not shown). Lastly, we tested whether reprogramming with BN1 and BN2 could convert neonatal human fibroblasts to neurons. Twenty days of reprogramming led to MAP2/TUJ1 positive cells with neuronal morphologies, that express ISL1 and lineage marker TRKA and TRKB, demonstrating that induction of iSNs is not restricted to embryonic fibroblasts (data not shown).

We additionally examined whether human iSNs exhibit membrane and electrophysiological properties of mature neurons. We performed whole-cell patch-clamp recordings.

Figure 7:
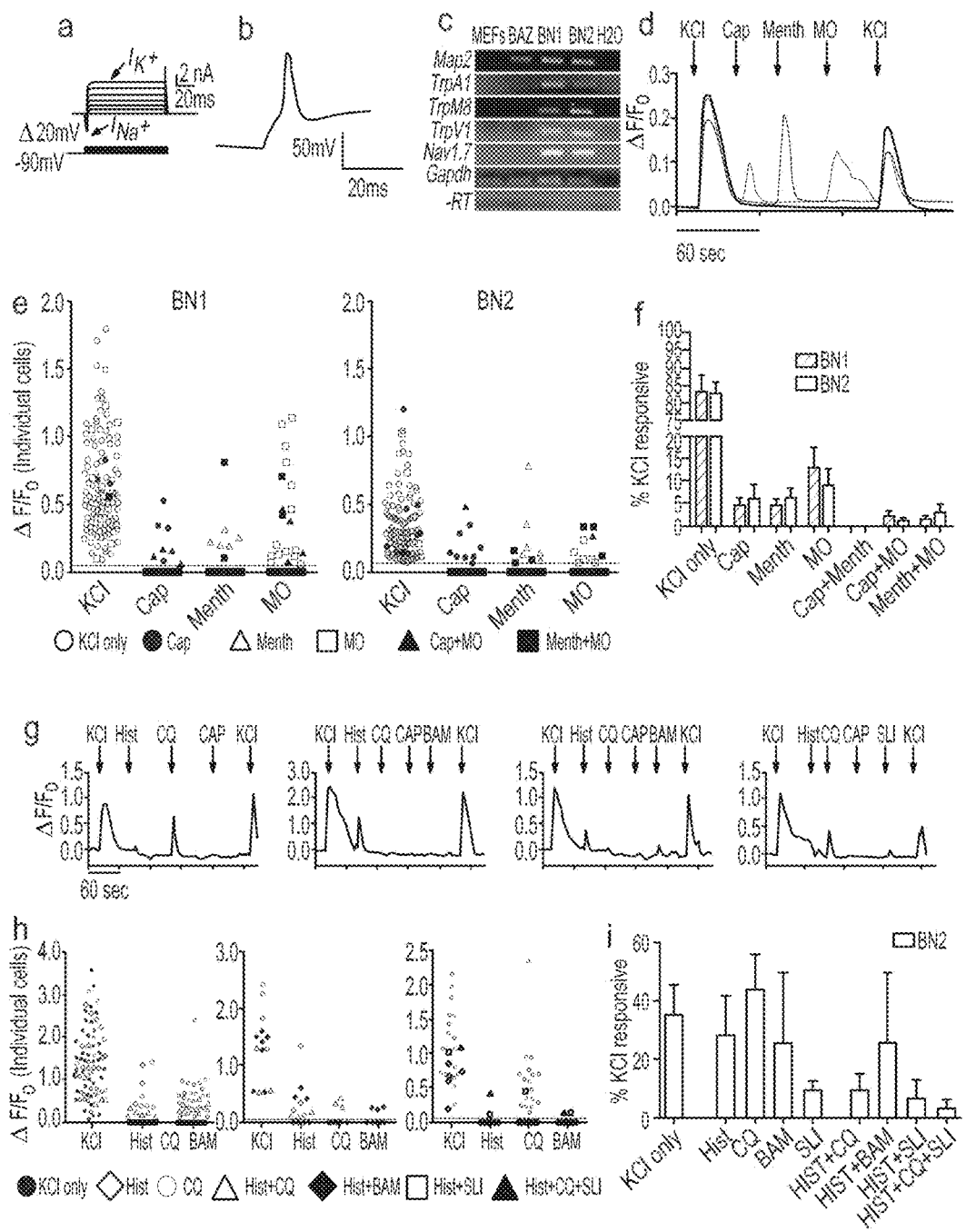

The average resting membrane potential of human iSNs was 40.067 mV (SEM=3.724, n=15). Depolarizing in voltage clamp mode elicited fast inward currents followed by slow outward currents consistent with opening of voltage-activated sodium and potassium channels, respectively (FIG. 7a). In addition, human iSNs were able to fire action potentials (FIG. 7b). Collectively, these data demonstrate human iSNs possess membrane and electrophysiological properties of functional neurons.

To determine whether human iSNs had acquired key characteristics of various subpopulations of nociceptive neurons we assessed expression of TRPA1, TRPM8, TRPV1 and NAV1.7 in HEFs, BAZ neurons and the iSNs. No expression of TRPA1, TRPM8, TRPV1 or NAV1.7 was detected in HEFs or BAZ neurons. In contrast, robust expression was observed in the human iSNs generated with both BN1 and BN2 (FIG. 7c). To determine if the TRP channels were functional, we performed calcium-imaging studies as previously described for the mouse iSNs. Human iSNs generated with either BN1 or BN2 exhibited rapid and selective calcium transients in response to capsaicin (BN1 4.4%±1.7 and BN2 5.9%±3.3); menthol (BN1 4.4%±1.4 and BN2 6.0%±2.3); mustard oil (BN1 12.8%±4.5 and BN2 8.8%±3.7). The majority of KCl responsive iSNs did not respond to any of the three ligands (BN1 83.1%±4.9 and BN2 82.6%±3.4) (FIGS. 7d and 7e). A few iSNs responded to two ligands sequentially: capsaicin and mustard oil (BN1 3.2%±0.7 and BN2 1.2%±1.2); menthol and mustard oil (BN1 1.9%±1.9 and BN2 1.1%±1.1). We did not detect any neurons that simultaneously responded to both capsaicin and menthol, or all three ligands. These calcium fluxes in response to ligand specific activation suggest that the channel receptors TRPA1, TRPM8, and TRPV1 are indeed functional though perhaps not co-expressed in similar numbers of cells as would expected based on in vivo studies (FIG. 7d-f).

We claim:

1. A method for generating induced sensory neurons (iSNs), comprising co-expressing Brn3A and Ngn1 genes via one or more expression vectors harboring Brn3A and Ngn1 genomic or cDNA sequences in a non-neuronal cell, thereby generating induced sensory neurons, wherein the non-neuronal cell is a fibroblast or a stem cell from a mammal.

2. The method of claim 1, wherein expression of the Brn3A/Ngn1 genes is temporal.

3. The method of claim 2, wherein temporal expression of the Brn3A/Ngn1 genes is via inducible expression.

4. The method of claim 1, wherein the non-neuronal cell is a fibroblast, an embryonic stem cell (ESC), or an induced pluripotent stem cell (iPSC).

5. The method of claim 1, wherein the non-neuronal cell is an embryonic fibroblast or an adult fibroblast.

6. The method of claim 1, wherein the mammal is human, mouse or rat.

7. The method of claim 1, wherein an expression vector harboring the Brn3A gene and the Ngn1 gene is introduced into the non-neuronal cell.

8. The method of claim 7, wherein the expression vector is a lentiviral vector.

9. The method of claim 1, further comprising detecting in the induced sensory neurons expression of one or more neuronal markers.

\* \* \* \* \*